(12) United States Patent
Yan et al.

(10) Patent No.: US 11,714,092 B2
(45) Date of Patent: *Aug. 1, 2023

(54) METHOD AND SYSTEM OF IDENTIFYING AND QUANTIFYING A PROTEIN

(71) Applicant: Regeneron Pharmaceuticals, Inc., Tarrytown, NY (US)

(72) Inventors: Yuetian Yan, Chappaqua, NY (US); Shunhai Wang, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/724,599

(22) Filed: Apr. 20, 2022

(65) Prior Publication Data
US 2022/0244270 A1 Aug. 4, 2022

Related U.S. Application Data

(63) Continuation of application No. 16/668,162, filed on Oct. 30, 2019, now Pat. No. 11,385,239.

(60) Provisional application No. 62/863,617, filed on Jun. 19, 2019, provisional application No. 62/753,633, filed on Oct. 31, 2018.

(51) Int. Cl.
*G01N 33/68* (2006.01)
*G01N 30/06* (2006.01)
*G01N 30/72* (2006.01)

(52) U.S. Cl.
CPC ......... *G01N 33/6854* (2013.01); *G01N 30/06* (2013.01); *G01N 30/7233* (2013.01)

(58) Field of Classification Search
CPC . G01N 33/6854; G01N 30/06; G01N 30/7233
USPC ................................ 250/281, 282, 283, 288
See application file for complete search history.

(56) References Cited

U.S. PATENT DOCUMENTS

| | | | |
|---|---|---|---|
| 11,385,239 B2 * | 7/2022 | Yan | ................... G01N 33/6854 |
| 2020/0225199 A1 | 7/2020 | Yan et al. | |

OTHER PUBLICATIONS

Wong Cintyu et al.: "Facile Method of Quantification for Oxidized Tryptophan Degradants of Monoclonal Antibody by Mixed Mode Ultra Performance Liquid Chromatography," Journal of Chromatography A., vol. 1270, Nov. 5, 2012, pp. 153-161.

Ya He et al.: "On-line Coupling of Size Exclusion Chromatography with Mixed-mode Liquid Chromatography for Comprehensive Profiling of Biopharmaceutical Drug Product," Journal of Chromatography A., vol. 1262, Sep. 10, 2012, pp. 122-129.

Xiaoyu Yang et al.: "Analysis and purification of IgG4 bispecific antibodies by a mixed-mode chromatography," Analytical Biochemistry vol. 484, Sep. 1, 2015 (Sep. 1, 2015), pp. 173-179.

Pavon Jorge Alexander et al.: "Analysis of monoclonal antibody oxidation by simple mixed mode chromatography," Jour Nal of Chromatography A, Elsevier, Amsterdam, NL, vol. 1431, Jan. 13, 2016, pp. 154-165.

(Continued)

*Primary Examiner* — Nicole M Ippolito
(74) *Attorney, Agent, or Firm* — Kramer Levin Naftalis & Frankel LLP

(57) ABSTRACT

Methods and system for identifying and/or quantifying a protein are provided herein.

20 Claims, 29 Drawing Sheets

(56) References Cited

OTHER PUBLICATIONS

Ehkirch Anthony et al: "Hyphenation of size exclusion chromatography to native ion mobility mass spectrometry for the analytical characterization of therapeutic antibodies and related products," Journal of Hromatography B: Biomedical Sciences & Applications, Elsevier, Amsterdam, NL, vol. 1086, Apr. 12, 2018 (Apr. 12, 2018), pp. 176-183.

Yuetian Yan et al: "Coupling Mixed-ModeSize Exclusion Chromatography with Native Mass Spectrometry for Sensitive Detection and Quantitation of Homodimer Impurities in Bispecific IgG," Analytical Chemistry, vol. 91, No. 17, Aug. 2, 2019.

International Search Report PCT Application Mo. PCT/US2019/058759, International Filing Date 30 Oct. 30, 2019, dated Nov. 2, 2020.

\* cited by examiner

⇐ Increasing precipitation ("salting-out") effect

Anions: $PO_4^{3-}$, $SO_4^{2-}$, $CH_3COO^-$, $Cl^-$, $Br^-$, $NO_3^-$, $ClO_4^-$, $I^-$, $SCN^-$ Cations: $NH_4^+$, $Rb^+$, $K^+$, $Na^+$, $Cs^+$, $Li^{2+}$, $Mg^{2+}$, $Ca^{2+}$, $Ba^{2+}$ Increasing chaotropic ("salting-in") effect ⇒

FIG. 3

METHOD AND SYSTEM OF IDENTIFYING AND QUANTIFYING A PROTEIN

CROSS-REFERENCE TO RELATED APPLICATIONS

This application is a continuation of U.S. patent application Ser. No. 16/668,162, filed on Oct. 30, 2019, which claims priority to and the benefit of U.S. Provisional Patent Application No. 62/863,617, filed on Jun. 19, 2019 and U.S. Provisional Patent Application No. 62/753,633, filed Oct. 31, 2018 which are each herein incorporated by reference.

FIELD

The invention generally pertains to a method and system of identifying and/or quantifying a protein.

BACKGROUND

Protein based biopharmaceutical products must meet very high standards of purity. There are several process-related impurities and product-related impurities that are found in biopharmaceuticals. These impurities do not have properties comparable to those of the desired product with respect to activity, efficacy, and safety. One example is post-translational modifications (PTMs) of the protein which profoundly affect protein properties relevant to their therapeutic application. Another such example includes the homodimeric contaminants that can be present during the production of bispecific antibody which ideally must be removed by downstream purification. These impurities could exhibit a different mode of action and potential toxicity or immunogenicity compared to the product. In addition, they can have a lower stability than the product which presents a higher risk for aggregation and immunogenicity. Despite the recent advances, the challenge to develop purity assay methods for quantitative evaluation of such impurities remains. Additionally, a key challenge in analytical method development for bispecific antibodies can be that the method must accurately and reproducibly detect impurities present at 2% or lower level relative to the main desired species. Therefore, it is important to monitor and characterize such impurities during different stages of drug development and production. Despite the importance of impurities for biological function, their study on a large scale has been hampered by a lack of suitable methods.

Analytical methods for purity assays must display sufficient accuracy and resolution to detect and quantify desired product and their impurities. Evaluation of impurities, such as PTMs in antibodies and homodimers in bispecific antibodies, can be difficult due to similarities between structural and physicochemical properties of such impurities and the desired product. Direct analysis of such impurities requires isolation of the desired product in a sufficiently large amount for the assay which is undesirable and only been possible in selected cases.

Thus, there is a long felt need in the art for a method and/or system for identifying and quantifying a protein—impurities and/or the desired product in a protein based biopharmaceuticals.

SUMMARY

Growth in the development, manufacture and sale of protein-based biopharmaceutical products has led to an increasing demand for method and/or system for identification and quantification of impurities in the products.

Embodiments disclosed herein satisfy the aforementioned demands by providing methods and systems for the rapid characterization of proteins.

The disclosure, at least in part, provides a method for quantifying an impurity in a sample.

In one exemplary embodiment, the method can comprise contacting the sample to a chromatographic system having a mixed-mode size exclusion chromatography resin with an additional functionality, washing the mixed-mode size exclusion chromatography resin using a mobile phase to provide an eluent including the impurity, and quantifying an amount of the impurity in the eluent using a mass spectrometer.

In one aspect of this embodiment, the method for quantifying an impurity in a sample can comprise contacting said sample to a chromatographic system having a mixed-mode size exclusion chromatography resin with a hydrophobic interaction functionality In one aspect of this embodiment, the method for quantifying an impurity in a sample can comprise contacting said sample to a chromatographic system having a mixed-mode size exclusion chromatography resin with a charge-charge interaction functionality.

In one aspect of this embodiment, the method for quantifying an impurity in a sample can comprise contacting about 10 μg to about 100 μg of a sample to a chromatographic system having a mixed-mode size exclusion chromatography resin with an additional functionality.

In one aspect of this embodiment, the method for quantifying an impurity in a sample can comprise washing the mixed-mode size exclusion chromatography resin using a mobile phase to provide an eluent including the impurity.

In one aspect of this embodiment, the method for quantifying an impurity in a sample can comprise washing the mixed-mode size exclusion chromatography resin using a mobile phase that can be compatible with a mass spectrometer.

In one aspect of this embodiment, the method for quantifying an impurity in a sample can comprise washing the mixed-mode size exclusion chromatography resin using a mobile phase, wherein the mobile phase can be selected from ammonium acetate, ammonium bicarbonate, or ammonium formate, or combinations thereof.

In one aspect of this embodiment, the method for quantifying an impurity in a sample can comprise washing the mixed-mode size exclusion chromatography resin using a mobile phase containing up to 600 mM total salt concentration.

In one aspect of this embodiment, the method for quantifying an impurity in a sample can comprise washing the mixed-mode size exclusion chromatography resin using a mobile phase with a flow rate of 0.2 ml/min to 0.4 ml/min.

In one aspect of this embodiment, the method for quantifying an impurity can comprise contacting the sample to a chromatographic system having a mixed-mode size exclusion chromatography resin with an additional functionality, wherein the impurity can be a product-related impurity.

In one aspect of this embodiment, the method for quantifying an impurity can comprise contacting the sample to a chromatographic system having a mixed-mode size exclusion chromatography resin with an additional functionality, wherein the impurity can be a process-related impurity.

In one aspect of this embodiment, the method for quantifying an impurity can comprise contacting the sample to a chromatographic system having a mixed-mode size exclusion chromatography resin with an additional functionality, wherein the impurity can be a degradation product of a protein.

In one aspect of this embodiment, the method for quantifying an impurity can comprise contacting the sample to a chromatographic system having a mixed-mode size exclusion chromatography resin with an additional functionality, wherein the impurity can be a digestion product of a protein.

In one aspect of this embodiment, the method for quantifying an impurity can comprise contacting the sample to a chromatographic system having a mixed-mode size exclusion chromatography resin with an additional functionality, wherein the impurity can be a homodimer species of a multispecific antibody product.

In one aspect of this embodiment, the method for quantifying an impurity can comprise contacting the sample to a chromatographic system having a mixed-mode size exclusion chromatography resin with an additional functionality, wherein the impurity can be a post-translational modification of a protein.

In one aspect of this embodiment, the method for quantifying an impurity can comprise quantifying an amount of the impurity in said eluent using a mass spectrometer, wherein the mass spectrometer can be a tandem mass spectrometer.

In one aspect of this embodiment, the method for quantifying an impurity can comprise quantifying an amount of the impurity in said eluent using a mass spectrometer, wherein the mass spectrometer can be a native mass spectrometer.

This disclosure, at least in part, provides a method for detecting an impurity in a sample.

In one exemplary embodiment, the method can comprise contacting the sample to a chromatographic system having a mixed-mode size exclusion chromatography resin with an additional functionality, washing the mixed-mode size exclusion chromatography resin using a mobile phase to provide an eluent including the impurity, and quantifying an amount of the impurity in the eluent using a mass spectrometer.

In one aspect of this embodiment, the method for detecting an impurity in a sample can comprise contacting said sample to a chromatographic system having a mixed-mode size exclusion chromatography resin with a hydrophobic interaction functionality In one aspect of this embodiment, the method for detecting an impurity in a sample can comprise contacting said sample to a chromatographic system having a mixed-mode size exclusion chromatography resin with a charge-charge interaction functionality.

In one aspect of this embodiment, the method for detecting an impurity in a sample can comprise contacting about 10 µg to about 100 µg of a sample to a chromatographic system having a mixed-mode size exclusion chromatography resin with an additional functionality.

In one aspect of this embodiment, the method for detecting an impurity in a sample can comprise washing the mixed-mode size exclusion chromatography resin using a mobile phase to provide an eluent including the impurity.

In one aspect of this embodiment, the method for detecting an impurity in a sample can comprise washing the mixed-mode size exclusion chromatography resin using a mobile phase that can be compatible with a mass spectrometer.

In some specific exemplary embodiments, the method for detecting an impurity in a sample can comprise washing the mixed-mode size exclusion chromatography resin using a mobile phase, wherein the mobile phase can be selected from ammonium acetate, ammonium bicarbonate, or ammonium formate, or combinations thereof.

In some specific exemplary embodiments, the method for detecting an impurity in a sample can comprise washing the mixed-mode size exclusion chromatography resin using a mobile phase containing up to 600 mM total salt concentration.

In one aspect of this embodiment, the method for detecting an impurity in a sample can comprise washing the mixed-mode size exclusion chromatography resin using a mobile phase with a flow rate of 0.2 ml/min to 0.4 ml/min.

In one aspect of this embodiment, the method for detecting an impurity can comprise contacting the sample to a chromatographic system having a mixed-mode size exclusion chromatography resin with an additional functionality, wherein the impurity can be a product-related impurity.

In one aspect of this embodiment, the method for detecting an impurity can comprise contacting the sample to a chromatographic system having a mixed-mode size exclusion chromatography resin with an additional functionality, wherein the impurity can be a process-related impurity.

In one aspect of this embodiment, the method for detecting an impurity can comprise contacting the sample to a chromatographic system having a mixed-mode size exclusion chromatography resin with an additional functionality, wherein the impurity can be a degradation product of a protein.

In one aspect of this embodiment, the method for detecting an impurity can comprise contacting the sample to a chromatographic system having a mixed-mode size exclusion chromatography resin with an additional functionality, wherein the impurity can be a digestion product of a protein.

In one aspect of this embodiment, the method for detecting an impurity can comprise contacting the sample to a chromatographic system having a mixed-mode size exclusion chromatography resin with an additional functionality, wherein the impurity can be a homodimer species of a multispecific antibody product.

In one aspect of this embodiment, the method for detecting an impurity can comprise contacting the sample to a chromatographic system having a mixed-mode size exclusion chromatography resin with an additional functionality, wherein the impurity can be a post-translational modification of a protein.

In one aspect of this embodiment, the method for detecting an impurity can comprise detecting an amount of the impurity in eluent using a mass spectrometer, wherein the mass spectrometer can be a tandem mass spectrometer.

In one aspect of this embodiment, the method for detecting an impurity can comprise detecting an amount of the impurity in said eluent using a mass spectrometer, wherein the mass spectrometer can be a native mass spectrometer.

This disclosure, at least in part, provides a method for detecting and/or quantifying a target protein in a sample.

In one exemplary embodiment, the method can comprise contacting the sample to a chromatographic system having a mixed-mode size exclusion chromatography resin with an additional functionality, washing the mixed-mode size exclusion chromatography resin using a mobile phase to provide an eluent including the target protein, and detecting and/or quantifying an amount of the target protein in the eluent using a mass spectrometer.

In one aspect of this embodiment, the method for detecting and/or quantifying a target protein in a sample can comprise contacting said sample to a chromatographic system having a mixed-mode size exclusion chromatography resin with a hydrophobic interaction functionality In one aspect of this embodiment, the method for detecting and/or quantifying a target protein in a sample can comprise contacting said sample to a chromatographic system having a mixed-mode size exclusion chromatography resin with a charge-charge interaction functionality.

In one aspect of this embodiment, the method for detecting and/or quantifying a target protein in a sample can comprise contacting about 10 μg to about 100 μg of a sample to a chromatographic system having a mixed-mode size exclusion chromatography resin with an additional functionality.

In one aspect of this embodiment, the method for detecting and/or quantifying a target protein in a sample can comprise washing the mixed-mode size exclusion chromatography resin using a mobile phase to provide an eluent including the impurity.

In one aspect of this embodiment, the method for detecting and/or quantifying a target protein in a sample can comprise washing the mixed-mode size exclusion chromatography resin using a mobile phase that can be compatible with a mass spectrometer. In a specific aspect, the method for detecting and/or quantifying a target protein in a sample can comprise washing the mixed-mode size exclusion chromatography resin using a mobile phase, wherein the mobile phase can be selected from ammonium acetate, ammonium bicarbonate, or ammonium formate, or combinations thereof. In another specific aspect, the method for detecting and/or quantifying a target protein in a sample can comprise washing the mixed-mode size exclusion chromatography resin using a mobile phase containing up to 600 mM total salt concentration.

In one aspect of this embodiment, the method for detecting and/or quantifying a target protein in a sample can comprise washing the mixed-mode size exclusion chromatography resin using a mobile phase with a flow rate of 0.2 ml/min to 0.4 ml/min.

In one aspect of this embodiment, the method for detecting and/or quantifying a target protein can comprise contacting the sample to a chromatographic system having a mixed-mode size exclusion chromatography resin with an additional functionality, wherein the target protein can be an antibody.

In one aspect of this embodiment, the method for detecting and/or quantifying a target protein can comprise contacting the sample to a chromatographic system having a mixed-mode size exclusion chromatography resin with an additional functionality, wherein the target protein can be a bispecific antibody.

In one aspect of this embodiment, the method for detecting and/or quantifying a target protein can comprise contacting the sample to a chromatographic system having a mixed-mode size exclusion chromatography resin with an additional functionality, wherein the target protein can be a therapeutic protein.

In one aspect of this embodiment, the method for detecting and/or quantifying a target protein can comprise contacting the sample to a chromatographic system having a mixed-mode size exclusion chromatography resin with an additional functionality, wherein the target protein can be an impurity.

In one aspect of this embodiment, the method for detecting and/or quantifying a target protein can comprise contacting the sample to a chromatographic system having a mixed-mode size exclusion chromatography resin with an additional functionality, wherein the target protein can be a process-related impurity of a biopharmaceutical process of manufacturing a protein.

In one aspect of this embodiment, the method for detecting and/or quantifying a target protein can comprise contacting the sample to a chromatographic system having a mixed-mode size exclusion chromatography resin with an additional functionality, wherein the target protein can be a product-related impurity of a biopharmaceutical process of manufacturing a protein.

In one aspect of this embodiment, the method for detecting and/or quantifying a target protein can comprise contacting the sample to a chromatographic system having a mixed-mode size exclusion chromatography resin with an additional functionality, wherein the target protein can be a degradation product of a protein.

In one aspect of this embodiment, the method for detecting and/or quantifying a target protein can comprise contacting the sample to a chromatographic system having a mixed-mode size exclusion chromatography resin with an additional functionality, wherein the target protein can be a digestion product of a protein.

In one aspect of this embodiment, the method for detecting and/or quantifying a target protein can comprise contacting the sample to a chromatographic system having a mixed-mode size exclusion chromatography resin with an additional functionality, wherein the target protein can be a homodimer species of a multispecific antibody product.

In one aspect of this embodiment, the method for detecting and/or quantifying a target protein can comprise quantifying an amount of the target protein in said eluent using a mass spectrometer, wherein the mass spectrometer can be a tandem mass spectrometer.

In one aspect of this embodiment, the method for detecting and/or quantifying a target protein can comprise quantifying an amount of the target protein in said eluent using a mass spectrometer, wherein the mass spectrometer can be a native mass spectrometer.

In one exemplary embodiment, this disclosure, at least in part, provides a mixed-mode chromatographic system a chromatographic column having a mixed-mode size exclusion chromatography resin with an additional functionality and a mass spectrometer.

In one aspect of this embodiment, the mixed-mode chromatographic system can comprise a mixed-mode size exclusion chromatography resin with hydrophobic interaction functionality.

In one aspect of this embodiment, the mixed-mode chromatographic system can comprise a mixed-mode size exclusion chromatography resin with charge-charge interaction functionality.

In one aspect of this embodiment, the mixed-mode chromatographic system can comprise a mixed-mode size exclusion chromatography resin with an additional functionality which can be used for elution of about 10 μg to about 100 μg of a sample.

In one aspect of this embodiment, the mixed-mode chromatographic system can comprise a mixed-mode size exclusion chromatography resin capable of receiving a mobile phase.

In one aspect of this embodiment, the mixed-mode chromatographic system can comprise a mixed-mode size exclusion chromatography resin further capable of receiving a sample having a target protein.

In one aspect of this embodiment, the mixed-mode chromatographic system can comprise a mixed-mode size exclusion chromatography resin capable of being washed with a mobile phase.

In one aspect of this embodiment, the mixed-mode chromatographic system can comprise a mass spectrometer coupled to a chromatographic column having a mixed-mode size exclusion chromatography resin with an additional functionality.

In one aspect of this embodiment, the mixed-mode chromatographic system can comprise a tandem mass spectrometer.

In one aspect of this embodiment, the mixed-mode chromatographic system can comprise a native spectrometer.

In one aspect of this embodiment, the mixed-mode chromatographic system can comprise a chromatographic column having a mixed-mode size exclusion chromatography resin with an additional functionality, wherein the mixed-mode size exclusion chromatography resin can be compatible with a mobile phase selected from ammonium acetate, ammonium bicarbonate, or ammonium formate, or combinations thereof.

In one aspect of this embodiment, the mixed-mode chromatographic system can comprise a chromatographic column having a mixed-mode size exclusion chromatography resin with an additional functionality, wherein the mixed-mode size exclusion chromatography resin can be washed using a mobile phase containing up to 600 mM total salt concentration.

In one aspect of this embodiment, the mixed-mode chromatographic system can comprise a chromatographic column having a mixed-mode size exclusion chromatography resin with an additional functionality, wherein the chromatographic column can be washed with a mobile phase with a flow rate of 0.2 ml/min to 0.4 ml/min.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows the Hofmeister series showing the effect of anions and cations on protein precipitation (or promoting hydrophobic interaction).

DETAILED DESCRIPTION

Impurities in biopharmaceuticals can cause changes that could potentially impact the efficacy, clearance, safety, and immunogenicity of the desired product. For example, oxidation of methionine and tryptophan side chains can affect antibody binding to Fc receptors and antigens (Bertolotti-Ciarlet et al. Mol. Immunol. (2009) 46: 1878-1882; Pan et al. Protein Sci. (2009) 18: 424-433; Wei et al. Anal. Chem. (2007) 79: 2797-2805; and Wang et al. Mol. Immunol. (2011) 48: 860-866).

Traditional separation-based antibody purity assays such as electrophoresis- and high-performance liquid chromatography (HPLC)-based methods lack the resolution needed to distinguish these impurities from the desired product. Peptide mapping via reverse phase liquid chromatography (RPLC) coupled with mass spectrometry used to monitor PTMs has some limitations as the sample preparation process for RP-LC-MS is lengthy, and in some cases the chromatographic conditions such as high temperature, organic solvents, and acidic pH could induce oxidation artifacts.

Figure 1:
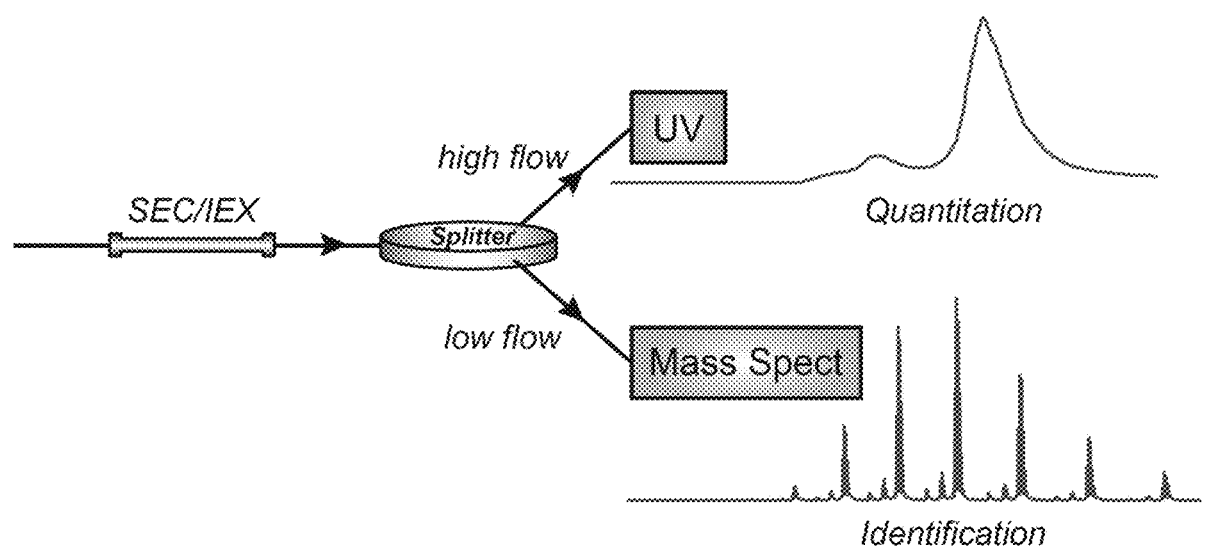
FIG. 1 shows represents an example of a system used for quantifying and/or detecting a protein using size exclusion chromatography or ion exchange chromatography.

Additionally, some size exclusion chromatography or ion exchange chromatography methods can also be used for separating impurities from the desired product. The separated impurities and the desired product can further be analyzed using a mass spectrometer. However, the mobile phase from the size exclusion chromatography or ion exchange chromatography column cannot be directly injected into the mass spectrometer and requires additional steps including a change in the mobile phase (See FIG. 1).

Considering the limitations of existing methods, an effective and efficient method for identification and quantification of impurities using a novel mixed-mode—size exclusion chromatography—mass spectrometry system was developed as disclosed herein. The mixed-mode—size exclusion chromatography—mass spectrometry system improves the sensitivity and ability to quantify impurities present at very low levels due to efficient mixed-mode separation and sensitive online MS detection which cannot be achieved by other typical assays.

Unless defined otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

Target Protein

Biopharmaceutical products are required to show high levels of potency, purity, and low level of structural heterogeneity. Structural heterogeneity often affects the bioactivity and efficacy of a drug. Therefore, characterizing and quantifying the therapeutic protein and/or the impurities is important in pharmaceutical drug development. Structural heterogeneity in a protein can arise from post-translational modifications as well as inherent chemical modifications during manufacturing and storage conditions. For proteins produced in the biotechnology industry, complementary separation techniques can be necessary both to purify the target protein and to give an accurate picture of the quality of the final product. The complexity of the product eliminates the use of simple one-dimensional separation strategies. Therefore, an accurate and efficient method of detecting and/or quantifying the therapeutic protein and/or impurities is needed.

In some exemplary embodiments, the disclosure provides a method for quantifying and/or detecting a protein and/or an impurity in a sample.

As used herein, the term "protein" includes any amino acid polymer having covalently linked amide bonds. Proteins comprise one or more amino acid polymer chains, generally known in the art as "polypeptides". "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides' refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Biotechnol. Genet. Eng. Rev. (2012) 147-75). In some embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins.

In some exemplary embodiments, the protein can be an antibody, a bispecific antibody, a multispecific antibody, antibody fragment, monoclonal antibody, or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')$_2$ fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment contains sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

Figure 2:
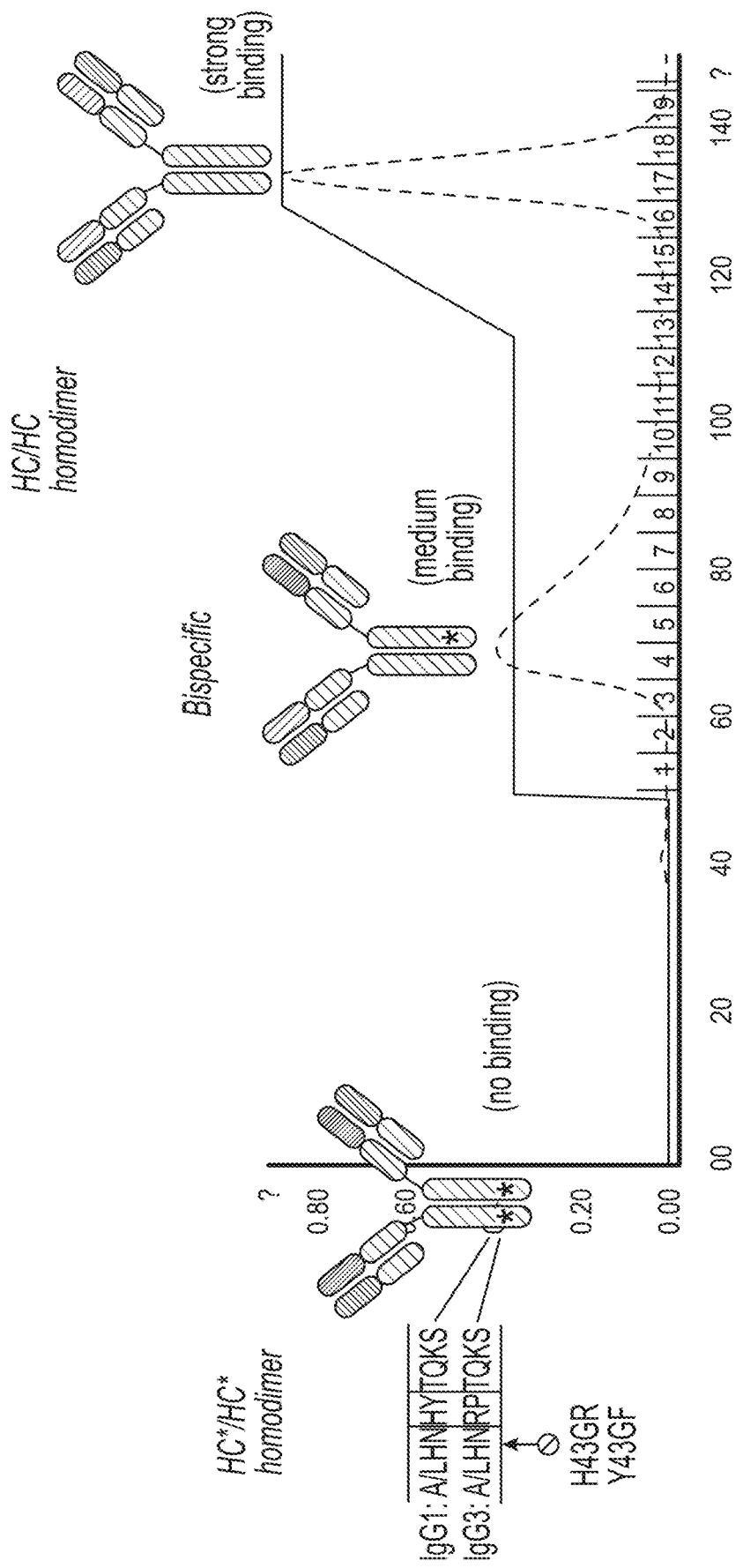
FIG. 2 represents an attempt for purifying a bispecific antibody from homodimer species using an exemplary embodiment.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bispecific antibody has two heavy chains each having three heavy chain CDRs, followed by a $C_H1$ domain, a hinge, a $C_H2$ domain, and a $C_H3$ domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats, such as, but not limited to triomab, knobs into holes IgG (kih IgG), crossMab, orth-Fab IgG, Dual-variable domains Ig (DVD-Ig), Two-in-one or dual action Fab (DAF), IgG-single-chain Fv (IgG-scFv), or κλ-bodies. The non-IgG-like different formats include Tandem scFvs, Diabody format, Single-chain diabody, tandem diabodies (TandAbs), Dual-affinity retargeting molecule (DART), DART-Fc, nanobodies, or antibodies produced by the dock-and-lock (DNL) method. Fan et al. and Kontermann and Brinkmann present a detailed review on bispecific antibody (Fan et al. "Bispecific antibodies and their applications" J. Hematol. Oncol. (2015) 8:130; Kontermann and Brinkmann. "Bispecific antibodies" Drug Discov. Today (2015) 20: 838-847). The methods of producing BsAbs are not limited to quadroma technology based on the somatic fusion of two different hybridoma cell lines, chemical conjugation, which involves chemical cross-linkers, and genetic approaches utilizing recombinant DNA technology. Examples of bsAbs include those disclosed in the following patent applications, which are hereby incorporated by reference in their entirety: U.S. Pat. No. 8,586,713, filed Jun. 25, 2010; U.S. Pat. Publication No. 2013/0045492, filed Jun. 5, 2012; U.S. Pat. No. 9,657,102, filed Sep. 19, 2013; U.S. Pat. Publication No. 2016/0024147, filed Jul. 24, 2015; U.S. Pat. Publication No. 2018/0112001, filed Sep. 22, 2017; U.S. Pat. Publication No. 2018/0104357, field Sep. 22, 2017; U.S. Pat. Publication No. 2017/0174779, filed Dec. 21, 2016; U.S. Pat. Publication No. 2017/0174781, filed Dec. 21, 2016; U.S. Pat. No. 10,179,819, zxfiled Jul. 29, 2016; and U.S. Pat. Publication No. 2018/0134794, filed Nov. 15, 2017. Low levels of homodimer impurities can be present at several steps during the manufacturing of bispecific antibodies. The detection of such homodimer impurities can be challenging when performed using intact mass analysis due to low abundances of the homodimer impurities and the co-elution of these impurities with main species when carried out using a regular liquid chromatographic method (as illustrated in FIG. 2).

Therapeutic bispecific antibodies (bsAbs) can simultaneously bind to two distinct targets and hold the promise to achieve enhanced therapeutic efficacy by offering dual functionality or novel mechanisms of action (Marie Godar et al., *Therapeutic bispecific antibody formats: a patent applications review (1994-2017)*, 28 EXPERT OPINION ON THERAPEUTIC PATENTS 251-276 (2018)). To date, more than 60 bispecific molecules have been developed and evaluated to treat various diseases, many of which adopt an IgG-like architecture due to its known advantages (stability, serum half-life, etc.) in therapeutic applications (Christoph Spiess, Qianting Zhai & Paul J. Carter, *Alternative molecular formats and therapeutic applications for bispecific antibodies*, 67 MOLECULAR IMMUNOLOGY 95-106 (2015); M X Sliwkowski & I Mellman, *Antibody therapeutics in cancer.*, 341 SCIENCE 1192-1198 (2013); Paul J. Carter, *Potent antibody therapeutics by design*, 6 NATURE REVIEWS IMMUNOLOGY 343-357 (2006)). Bispecific antibodies are frequently produced in a single cell by co-expressing different light and heavy chains. Subsequently, assembly of the bsAb construct requires correct pairing of cognate light and heavy chains, as well as heterodimerization of two different half-molecules. Unfortunately, this process can also result in the formation of misassembled molecular constructs, such as monospecific molecules (e.g., homodimer species). Unlike other impurities, removal of homodimer species through down-stream purification can be challenging, as they often exhibit highly similar physicochemical properties to the anticipated bsAb products. To improve the fidelity of polypeptide chain pairing and therefore favoring the formation of bsAbs, various strategies have been developed in recent years (Shixue Chen et al., *Immunoglobulin Gamma-Like Therapeutic Bispecific Antibody Formats for Tumor Therapy*, 2019 JOURNAL OF IMMUNOLOGY RESEARCH 1-13 (2019)). For example, the use of an identical light chain for each antigen-binding arm of the bsAb has been particularly successful to avoid the mispairing between light and heavy chains (A. Margaret Merchant et al., *An efficient route to human bispecific IgG*, 16 NATURE BIOTECHNOLOGY 677-681 (1998)). In addition, the hetero-dimerization of different heavy chains can be greatly facilitated using a knobs-into-holes (John B. b. Ridgway, Leonard G. Presta & Paul Carter, '*Knobs-into-holes' engineering of antibody CH3 domains for heavy chain heterodimerization*, 9 "PROTEIN ENGINEERING, DESIGN AND SELECTION" 617-621 (1996)) design, where specific mutations were engineered into the Fc portion of the antibody to favor heterodimer formation. Alternatively, by modulating the Protein A binding affinity via amino acid substitutions in the Fc portion, a bsAb can also be effectively isolated from homodimer impurities during the Protein A purification step (Adam Zwolak et al., *Rapid Purification of Human Bispecific Antibodies via Selective Modulation of Protein A Binding*, 7 SCIENTIFIC REPORTS 15521 (2017)). This strategy has already been successfully implemented to achieve mass production of bsAbs to support clinical studies (Andrew D. Tustian et al., *Development of purification processes for fully human bispecific antibodies based upon modification of protein A binding avidity*, 8 mAbs 828-838 (2016)).

Advances in novel bsAb formats through protein engineering and process development have enabled large scale production of therapeutic bsAbs with high purity. However, the presence of low-abundance homodimer impurities in bsAb drug products can be still possible and needs to be routinely monitored during development and in release testing. Regarded as product-related impurities, homodimer antibodies can be highly similar to the desired bsAb in many properties, rendering their detection and quantitation a unique and challenging task for current analytical techniques. As homodimer species usually exhibit distinctive molecular weights compared to the corresponding bsAb, mass measurement at the intact protein level using LC-MS-based techniques has been the method-of-choice for their characterization (R. Jeremy Woods et al., *LC-MS characterization and purity assessment of a prototype bispecific antibody*, 5 mAbs 711-722 (2013); Wolfgang Schaefer et al., *Heavy and light chain pairing of bivalent quadroma and knobs-into-holes antibodies analyzed by UHR-ESI-QTOF mass spectrometry*, 8 mAbs 49-55 (2015); Frank D. Macchi et al., *Absolute Quantitation of Intact Recombinant Antibody Product Variants Using Mass Spectrometry*, 87 ANALYTICAL CHEMISTRY 10475-10482 (2015); Luis Schachner et al., *Characterization of Chain Pairing Variants of Bispecific IgG Expressed in a Single Host Cell by High Resolution Native and Denaturing Mass Spectrometry*, 88 ANALYTICAL CHEMISTRY 12122-12127 (2016); Yiyuan Yin et al., *Precise quantification of mixtures of bispecific IgG produced in single host cells by liquid chromatography-Orbitrap high-resolution mass spectrometry*, 8 mAbs 1467-1476 (2016); Chunlei Wang et al., *A systematic approach for analysis and characterization of mispairing in bispecific antibodies with asymmetric architecture*, 10 mAbs 1226-1235 (2018); Markus Haberger et al., *Rapid characterization of biotherapeutic proteins by size-exclusion chromatography coupled to native mass spectrometry*, 8 mAbs 331-339 (2015); Francois Debaene et al., *Time Resolved Native Ion-Mobility Mass Spectrometry to Monitor Dynamics of IgG4 Fab Arm Exchange and "Bispecific" Monoclonal Antibody Formation*, 85 ANALYTICAL CHEMISTRY 9785-9792 (2013)). For example, the use of reversed phase chromatography (RPLC) coupled to a high-resolution accurate-mass (HRAM) mass spectrometer has been reported by several labs to quantify homodimer impurities in bsAb samples (Woods et al, 2013, supra; Schachner et al, 2016, supra; Yin et al, 2016, supra). In most of these studies, the homodimer impurities could be detected and quantified without chromatographic separation from the main bsAb species. Indeed, considering the large size (~150 kDa) as well as the similarity in physicochemical properties, it can often be a challenging task to achieve sufficient separation between homodimer antibodies and bsAb using the RPLC method. As a result, RPLC-MS-based methods are frequently lacking sensitivity in detecting homodimer species present at low levels (the lowest LLOQ reported is ~1% (Schachner et al, 2016, supra; Yin et al, 2016, supra), largely due to ion suppression from the co-eluting and overwhelmingly more abundant bsAb species. Moreover, without chromatographic separation, detection of homodimer species with molecular weights close to bsAb can be particularly challenging, as variant forms of the bsAb from PTMs (e.g., +128 Da for C-terminal Lys and +162 for glycation) or adduction formation, could potentially interfere with the analysis. Finally, in cases where chromatographic separation between homodimer and bsAb is achieved by the RPLC method, MS-based quantitation could still be compromised by the discrepancy in ionization efficiency of antibodies eluting at different retention times within different solvent compositions, which requires generating an external calibration curve using spiked-in standards when performing quantitation (Risto Kostiainen & Tiina J. Kauppila, *Effect of eluent on the ionization process in liquid chromatography-mass spectrometry*, 1216 JOURNAL OF CHROMATOGRAPHY A 685-699 (2009)). Alternatively, native mass spectrometry represents another valuable technique in the analysis of intact proteins and has been integrated into many routine analytical workflows for monoclonal antibody (mAb) heterogeneity assessment (Haberger et al, 2016, supra; Sara Rosati et al., *Qualitative and Semiquantitative Analysis of Composite Mixtures of Antibodies by Native Mass Spectrometry*, 84 ANALYTICAL CHEMISTRY 7227-7232 (2012); Anthony Ehkirch et al., *Hyphenation of size exclusion chromatography to native ion mobility mass spectrometry for the analytical characterization of therapeutic antibodies and related products*, 1086 JOURNAL OF CHROMATOGRAPHY B 176-183 (2018); Guillaume Terral, Alain Beck & Sarah Cianférani, *Insights from native mass spectrometry and ion mobility-mass spectrometry for antibody and antibody-based product characterization*, 1032 JOURNAL OF CHROMATOGRAPHY B 79-90 (2016); Oscar Hernandez-Alba et al., *Native Mass Spectrometry, Ion Mobility, and Collision-Induced Unfolding for Conformational Characterization of IgG4 Monoclonal Antibodies*, 90 ANALYTICAL CHEMISTRY 8865-8872 (2018)). Because of the more concentrated signal generated from fewer charge states, native MS can have an improved sensitivity over RPLC-MS. For example, Rosati et al. (supra) reported the use of native MS to study a binary mixture of two co-expressed IgG1 antibodies. However, without efficient chromatographic separation, detection and quantitation of homodimer species present at low levels continues to be challenging for the same reasons discussed above.

To date, there have been limited reports on analytical methods that rely on chromatographic separation for detection and quantitation of homodimer species in bsAb samples. For example, hydrophobic interaction chromatography (HIC) (Wang et al., 2018, supra) or ion exchange chromatography (IEX) (A. F. Labrijn et al., *Efficient generation of stable bispecific IgG1 by controlled Fab-arm exchange*, 110 PROCEEDINGS OF THE NATIONAL ACADEMY OF SCIENCES 5145-5150 (2013); Michael J Gramer et al., *Production of stable bispecific IgG1 by controlled Fab-arm exchange*, 5 mAbs 962-973 (2013)) have been shown to separate bsAb from its homodimers if they exhibit sufficiently different values in hydrophobicity or isoelectric point (pI), respectively. In addition, recent advances in online IEX-native MS technologies (Yuetian Yan et al., *Ultrasensitive Characterization of Charge Heterogeneity of Therapeutic Monoclonal Antibodies Using Strong Cation Exchange Chromatography Coupled to Native Mass Spectrometry*, 90 ANALYTICAL CHEMISTRY 13013-13020 (2018); Florian Füssl et al., *Charge Variant Analysis of Monoclonal Antibodies Using Direct Coupled pH Gradient Cation Exchange Chromatography to High Resolution Native Mass Spectrometry*, 90 ANALYTICAL CHEMISTRY 4669-4676 (2018); Aaron O. Bailey et al., *Charge variant native mass spectrometry benefits mass precision and dynamic range of monoclonal antibody intact mass analysis*, 10 mAbs 1214-1225 (2018)) provide an effective approach for sensitive detection of low-level homodimer species in bsAb. However, owing to the high resolution, IEX usually generates a complicated charge profile for each antibody based on their charge heterogeneity, which will likely overlap with each other. Moreover, MS-based quantitation using this approach can be complicated, as all of the separated charge variant forms from each molecule need to be summed up for calculation. In addition, similar to the RPLC-based approach, the IEX method utilizes a gradient elution, which will likely compromise MS-based quantitation due to different ionization efficiency of antibodies eluting under different solvent conditions (e.g., pH or salt concentrations). Recently, a SEC-based mixed-mode chromatography (MM-SEC) method, which separates analytes by both hydrodynamic volume and hydrophobic interactions with the column matrix, has been applied in studying antibody heterogeneity (Xiaoyu Yang et al., *Analysis and purification of IgG4 bispecific antibodies by a mixed-mode chromatography*, 484 ANALYTICAL BIOCHEMISTRY 173-179 (2015); Cintyu Wong, Camille Strachan-Mills & Sudhir Burman, *Facile method of quantification for oxidized tryptophan degradants of monoclonal antibody by mixed mode ultra performance liquid chromatography*, 1270 JOURNAL OF CHROMATOGRAPHY A 153-161 (2012); Jorge Alexander Pavon et al., *Analysis of monoclonal antibody oxidation by simple mixed mode chromatography*, 1431 JOURNAL OF CHROMATOGRAPHY A 154-165 (2016)). Coupled to UV or fluorescence detection, the MM-SEC method was successfully applied for relative quantitation of homodimer species in a bsAb sample (Yang et al, 2015, supra). However, it is clear that the utility of this method can be limited to cases where the homodimer and bsAb species are sufficiently different in hydrophobicity so that baseline separation can be achieved for UV- or fluorescence-based quantitation. Moreover, as the identification of homodimer species was solely based on retention time alignment against standards, there was always a risk of overestimation of relative abundance if they co-elute with the oligomeric or truncated forms of bsAb molecule.

The concept of mixed-mode chromatography using an SEC column originates from the unwanted secondary interactions between protein analytes and the column matrix. Ideally, SEC should separate protein analytes solely based on their hydrodynamic volume. In practice, electrostatic, hydrophobic and hydrogen-bonding interactions could all contribute to the retention and separation of proteins to different extents, depending on the column matrix, buffer conditions and protein characteristics (Alexandre Goyon et al., *Unraveling the mysteries of modern size exclusion chromatography—the way to achieve confident characterization of therapeutic proteins*, 1092 JOURNAL OF CHROMATOGRAPHY B 368-378 (2018); Tsutomu Arakawa et al., *The critical role of mobile phase composition in size exclusion chromatography of protein pharmaceuticals*, 99 JOURNAL OF PHARMACEUTICAL SCIENCES 1674-1692 (2010)). Utilizing these secondary interactions during SEC separation by properly optimizing the chromatographic conditions presents opportunities to improve separation of antibodies with similar hydrodynamic volume but different surface characteristics (e.g., charge and hydrophobicity). By using MS-compatible mobile phases, online coupling of mixed-mode SEC with native MS detection (MM-SEC-MS) can have many advantages over UV-based methods, including unambiguous identification of homodimer species by accurate mass measurements, minimal interference from co-eluting species and less stringent requirements on chromatographic resolution (Terral et al., 2016, supra; Goyon et al., 2017, supra).

As used herein "multispecific antibody" or "Mab" refers to an antibody with binding specificities for at least two different antigens. While such molecules normally will only bind two antigens (i.e. bispecific antibodies, BsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

During many stages of production of biopharmaceuticals, impurities can be formed. Biotechnology-derived impurities can be very difficult to characterize and quantify, because they often are present at very low levels, and because they can represent very complicated species or mixtures of species. It can be also very difficult to obtain an authentic reference standard of the impurity peaks. However, to fully characterize a trace amount of an impurity protein becomes a time consuming, lengthy, and often very expensive process. Often the impurity can include variants, isoforms, degradation products, product-related impurities, process-related, minor post translational modifications, aggregates, or clipped fragments of the intact recombinant protein. There are an almost infinite number of possible impurities, most of which might be known but not all.

As used herein, the term "target protein" can include the desired product or an impurity or both.

As used herein, the term "desired product" refers to the protein which has the desired structure, function, or efficacy profile.

As used herein, the term "impurity" can include any undesirable protein present in the biopharmaceutical product. Impurity can include process and product-related impurities. The impurity can further be of known structure, partially characterized, or unidentified. Process-related impurities can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables. Product-related impurities (e.g., precursors, certain degradation products) can be molecular variants arising during manufacture and/or storage that do not have properties comparable to those of the desired product with respect to activity, efficacy, and safety. Such variants may need considerable effort in isolation and characterization in order to identify the type of modification(s). Product-related impurities can include truncated forms, modified forms, and aggregates. Truncated forms are formed by hydrolytic enzymes or chemicals which catalyze the cleavage of peptide bonds. Modified forms include, but are not limited to, deamidated, isomerized, mismatched S—S linked, oxidized, or altered conjugated forms (e.g., glycosylation, phosphorylation). Modified forms can also include any post-translational modification form. Aggregates include dimers and higher multiples of the desired product. (Q6B Specifications: Test Procedures and Acceptance Criteria for Biotechnological/Biological Products, ICH August 1999, U.S. Dept. of Health and Humans Services).

As used herein, the general term "post-translational modifications" or "PTMs" refer to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g., methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See http://www.uniprot.org/docs/ptmlist for a more detailed controlled vocabulary of PTMs curated by UniProt.

Mixed Mode Size-Exclusion Chromatography

As used herein, the term "chromatography" refers to a process in which a chemical mixture carried by a liquid or gas can be separated into components as a result of differential distribution of the chemical entities as they flow around or over a stationary liquid or solid phase.

As used herein, the term "Mixed Mode Chromatography (MMC)" or "multimodal chromatography" includes a chromatographic method in which solutes interact with stationary phase through more than one interaction mode or mechanism. MMC can be used as an alternative or complementary tool to traditional reversed-phased (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Mixed mode chromatography media can provide unique selectivity that cannot be reproduced by single mode chromatography. Mixed mode chromatography can also provide potential cost savings and operation flexibility compared to affinity based methods.

The phrase "size exclusion chromatography" or "SEC" or "gel filtration" includes a liquid column chromatographic technique that can sort molecules according to their size in solution.

As used herein, the terms "SEC chromatography resin" or "SEC chromatography media" are used interchangeably herein and can include any kind of solid phase used in SEC which separates the impurity from the desired product (e.g., a homodimer contaminant for a bispecific antibody product). The volume of the resin, the length and diameter of the column to be used, as well as the dynamic capacity and flow-rate can depend on several parameters such as the volume of fluid to be treated, concentration of protein in the fluid to be subjected to the process of the invention, etc. Determination of these parameters for each step is well within the average skills of the person skilled in the art.

As used herein, the term "mixed-mode-size exclusion chromatography" or "MM-SEC" can include any chromatographic method which separates proteins through an additional interaction other than the separation based on their size. The additional or secondary interaction can exploit one or more of the following mechanisms: anion exchange, cation exchange, hydrophobic interaction, hydrophilic interaction, charge-charge interaction, hydrogen bonding, pi-pi bonding, and metal affinity. The mixed-mode-size exclusion chromatography resin can refer to any kind of solid phase used for MM-SEC separation. Non-limiting examples are Sepax Zenix SEC-300, Waters BEH 300, or Agilent Bio SEC-3.

As used herein, the term "hydrophobic functionality" refers to the hydrophobic interaction of the protein with the SEC chromatographic resin as a secondary interaction. The hydrophobic functionality can also significantly impact peak shape, which can have a pronounced effect on the resolving ability of the process. Hydrophobic interactions are strongest at high ionic strength of the mobile phase. For selecting a mobile phase to include hydrophobic functionality in a resin, various ions can be arranged in a so-called soluphobic series depending on whether they promote hydrophobic interactions (salting-out effects) or disrupt the structure of water (chaotropic effect) and lead to the weakening of the hydrophobic interaction (as illustrated in FIG. 3). Cations are ranked in terms of increasing salting out effect as $Ba^{++}$; $Ca^{++}$; $Mg^{++}$; $Li^+$; $Cs^+$; $Na^+$; $K^+$; $Rb^+$; $NH_4^+$, while anions may be ranked in terms of increasing chaotropic effect as $PO^-$; $SO_4^-$; $CH_3CO_2^-$; $Cl^-$; $Br^-$; $NO_3^-$; $ClO_4^-$; P; $SCN^-$. In general, Na, K or $NH_4$ sulfates effectively promote ligand-protein interaction in HIC. Salts may be formulated that influence the strength of the interaction as given by the following relationship: $(NH_4)_2SO_4 > Na_2SO_4 > NaCl > NH_4Cl > NaBr > NaSCN$.

Mass Spectrometry

As used herein, the term "mass spectrometer" includes a device capable of detecting specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

As used herein, the term "mass analyzer" includes a device that can separate species, that is, atoms, molecules, or clusters, according to their mass. Non-limiting examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

As used herein, the term "tandem mass spectrometry" includes a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MS$^n$ can be performed by first selecting and isolating a precursor ion (MS$^2$), fragmenting it, isolating a primary fragment ion (MS$^3$), fragmenting it, isolating a secondary fragment (MS$^4$), and so on as long as one can obtain meaningful information or the fragment ion signal is detectable. Tandem MS have been successfully performed with a wide variety of analyzer combinations. What analyzers to combine for a certain application is determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers.

In some exemplary embodiments, mass spectrometry can be performed under native conditions.

As used herein, the term "native conditions" or "native MS" or "native ESI-MS" can include a performing mass spectrometry under conditions that preserve non-covalent interactions in an analyte. For detailed review on native MS, refer to the review: Elisabetta Boeri Erba & Carlo Petosa, *The emerging role of native mass spectrometry in characterizing the structure and dynamics of macromolecular complexes*, 24 PROTEIN SCIENCE 1176-1192 (2015). Some of the distinctions between native ESI and regular ESI are illustrated in table 1 (Hao Zhang et al., *Native mass spectrometry of photosynthetic pigment-protein complexes*, 587 FEBS Letters 1012-1020 (2013)).

TABLE 1

|  | Native ESI | Regular ESI |
|---|---|---|
| Sample Solution | Aqueous solution water, ammonium acetate | Partial organic solution water, formic acid, acetonitrile/Methanol (pH 1-2) |
| Spray Condition | 10-50 nL/min Spray voltage 0.8-1.5 kV Temperatures 20-30° C. | 10-50 nL/min Spray voltage 0.8-1.5 kV Temperatures 20-30° C. |
| Salt Treatment | Offline Desalt | Online/Offline Desalt with RP-HPLC |
| Protein Concentration | 1-10 µM (complex) | <1 µM (subunit) |
| Output Information | Molecular weight of protein complex and subunit Non-covalent interactions Stoichiometry Structure | Molecular weight of a single subunit |

Exemplary Embodiments

Embodiments disclosed herein provide compositions, methods, and systems for the rapid characterization of proteins in a sample.

As used herein, the terms "include," "includes," and "including," are meant to be non-limiting and are understood to mean "comprise," "comprises," and "comprising," respectively.

The disclosure provides methods for detecting or quantifying an impurity in a sample comprising contacting the sample to a chromatographic system having a mixed-mode chromatography resin; washing the mixed-mode size exclusion chromatography resin using a mobile phase to provide an eluent including the impurity; and detecting the impurity in the eluent using a mass spectrometer.

The disclosure provides methods for detecting or quantifying a target protein in a sample comprising contacting the sample to a chromatographic system having a mixed-mode chromatography resin, washing the mixed-mode chromatography resin using a mobile phase to provide an eluent including the target protein, and detecting or quantifying the target protein in the eluent using a mass spectrometer.

In some specific exemplary embodiments, the chromatographic system can comprise a size exclusion chromatography resin with an additional interaction.

In some specific exemplary embodiments, the chromatographic system can comprise a size exclusion chromatography resin with a hydrophobic interaction functionality.

In some specific exemplary embodiments, the chromatographic system can comprise a size exclusion chromatography resin with a charge-charge interaction functionality.

In some exemplary embodiments, the method for detecting or quantifying an impurity in a sample can include an impurity which can include at least one undesirable protein. The impurity(s) can be of known structure, or be partially characterized, or be unidentified.

In some exemplary embodiments, the impurity can be a product-related impurity. The product related impurity can be molecular variants, precursors, degradation products, fragmented protein, digested product, aggregates, post-translational modification form, or combinations thereof.

In some specific exemplary embodiments, the impurity can be a process-related impurity. The process-related impurity can include impurities derived from the manufacturing process, i.e., nucleic acids and host cell proteins, antibiotics, serum, other media components, enzymes, chemical and biochemical processing reagents, inorganic salts, solvents, carriers, ligands, and other leachables used in the manufacturing process.

In some exemplary embodiments, the impurity can be a protein with a pI in the range of about 4.5 to about 9.0. In one aspect, the impurity can be a protein with a pI of about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In some exemplary embodiments, the impurity can be a homodimer species. In one aspect, the impurity can be a homodimer species, which can be formed during the production of a bispecific antibody. In another aspect, the number of impurities in the sample can be at least two.

In some exemplary embodiments, amount of the sample loaded on the chromatographic system can range from about 10 µg to about 100 µg. In one exemplary embodiment, the amount of the sample loaded on the chromatographic system can be about 10 µg, about 12.5 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg.

In some exemplary embodiments, the mobile phase used to elute the impurity can be a mobile phase that can be compatible with a mass spectrometer.

In some specific exemplary embodiments, the mobile phase can be ammonium acetate, ammonium bicarbonate, or ammonium formate, or combinations thereof. In one aspect, the total concentration of the mobile phase can range up to about 600 mM. In a specific aspect, the total concentration of the mobile phase can be about 5 mM, about 6 mM, 7 mM, about 8 mM, 9 mM, about 10 mM, 12.5 mM, about 15 mM, 17.5 mM, about 20 mM, 25 mM, about 30 mM, 35 mM, about 40 mM, 45 mM, about 50 mM, 55 mM, about 60 mM, 65 mM, about 70 mM, 75 mM, about 80 mM, 75 mM, about 95 mM, 100 mM, about 1100 mM, 120 mM, about 130 mM, 140 mM, about 150 mM, 160 mM, about 170 mM, 180 mM, about 190 mM, 200 mM, about 225 mM, 250 mM, about 275 mM, 300 mM, about 325 mM, 350 mM, about 375 mM, 400 mM, about 425 mM, 450 mM, about 475 mM, 500 mM, about 525 mM, 550 mM, about 575 mM, or about 600 mM.

In some exemplary embodiments, the mobile phase can have a flow rate of about 0.1 ml/min to about 0.4 ml/min. In one exemplary embodiment, the flow rate of the mobile phase can be about 0.1 ml/min, about 0.15 ml/min, about 0.20 ml/min, about 0.25 ml/min, about 0.30 ml/min, about 0.35 ml/min, or about 0.4 ml/min.

In some exemplary embodiments, the method for detecting or quantifying an impurity can comprise detecting or quantifying the impurity in eluent using a mass spectrometer. In one aspect, the mass spectrometer can be a tandem mass spectrometer. In another aspect, the mass spectrometer can comprise a nano-spray.

In some exemplary embodiments, the eluent can comprise a target protein in addition to the impurity. In one aspect, the target protein can include an antibody, bispecific antibody, antibody fragment, or a multispecific antibody. In a specific aspect, the target protein can be a monoclonal antibody. In a specific aspect, the target protein can be a therapeutic antibody. In a specific aspect, the target protein can be an immunoglobulin protein. In another specific aspect, immunoglobulin protein can be IgG1. In yet another specific aspect, immunoglobulin protein can be IgG4. In one aspect, the target protein can be a bispecific antibody. In a specific aspect, the bispecific antibody can be Anti-CD20/CD3 monoclonal antibody. In one aspect, the target protein can be an antibody generated using mouse fibroblast cell line MG87. In one aspect, the target protein can be an antibody fragment formed on digestion of the antibody.

In one aspect, the target protein can be a post-translationally modified protein. In a specific aspect, the post-translationally modified protein can be a formed by cleavage, N-terminal extensions, protein degradation, acylation of the N-terminus, biotinylation, amidation of the C-terminal, oxidation, glycosylation, iodination, covalent attachment of prosthetic groups, acetylation, alkylation, methylation, adenylation, ADP-ribosylation, covalent cross links within, or between, polypeptide chains, sulfonation, prenylation, Vitamin C dependent modifications, Vitamin K dependent modification, glutamylation, glycylation, glycosylation, deglycosylation, isoprenylation, lipoylation, phosphopantetheinylation, phosphorylation, sulfation, citrullination, deamidation, formation of disulfide bridges, proteolytic cleavage, ISGylation, SUMOylation or ubiquitination (covalent linkage to the protein ubiquitin).

In another aspect, the target protein can be a degradation product of a protein.

In yet another aspect, the target protein can be an impurity found in a biopharmaceutical product. In a specific aspect, the target protein can be an impurity found during the manufacture of the biopharmaceutical product.

In one aspect, the target protein can be a protein with a pI in the range of about 4.5 to about 9.0.

In one aspect, the target protein can be a product-related impurity. The product related impurity can be molecular variants, precursors, degradation products, fragmented protein, digested product, aggregates, post-translational modification form, or combinations thereof.

In one aspect, the target protein can be a process-related impurity. The process-related impurity can include impurities derived from the manufacturing process, i.e., nucleic acids and host cell proteins, antibiotics, serum, other media components, enzymes, chemical and biochemical processing reagents, inorganic salts, solvents, carriers, ligands, and other leachables used in the manufacturing process.

In one aspect, the number of impurities in the sample can be at least two.

In one aspect, the post-transnationally modified protein can be formed on oxidation of a protein.

In another aspect, the target protein can include a degradation product.

In another aspect, the degradation product can include a post-translation modification of a therapeutic protein.

In some exemplary embodiments, washing the mixed-mode chromatography resin using a mobile phase requires less than about 30 minutes. In one aspect, the time required for washing the mixed-mode chromatography resin using a mobile phase can be about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 26 minutes, about 27 minutes, about 28 minutes, about 29 minutes, or about 30 minutes.

In some exemplary embodiments, the chromatographic system can be used for at least about 3 sample runs without cleaning. In one aspect, the chromatographic system can be used for at least about 3 sample runs, at least about 4 sample runs, at least about 5 sample runs, at least about 6 sample runs, at least about 7 sample runs, or at least about 8 sample runs, without cleaning.

It is understood that the methods are not limited to any of the aforesaid protein, impurity, column and that the methods for detecting or quantifying may be conducted by any suitable means.

Figure 4:
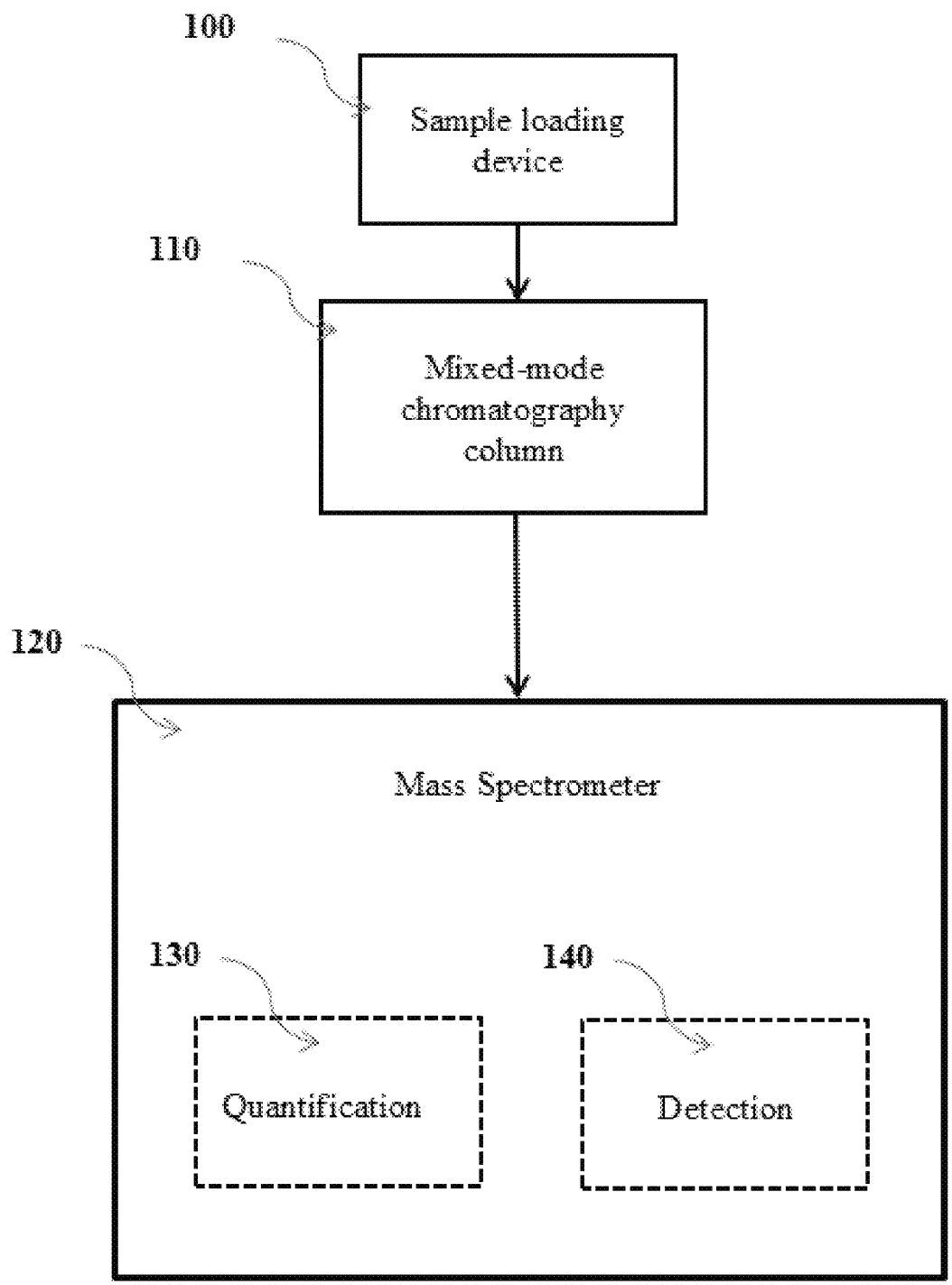
FIG. 4 shows a mixed-mode size exclusion chromatography mass spectrometry system according to an exemplary embodiment.

In some exemplary embodiments, the disclosure provides a mixed-mode chromatographic system comprising a chromatographic column 110 capable of being washed using a mobile phase to provide an eluent including a target protein and a mass spectrometer 120 coupled to the chromatographic column (as illustrated in FIG. 4). In one aspect, the chromatographic column 110 can be capable of being contacted with a sample using a sample loading device 100.

In some exemplary embodiments, the amount of the sample that can be loaded on the chromatographic column 110 can range from about 10 µg to about 100 µg. In one aspect, the amount of the sample that can be loaded on the chromatographic column 110 can be about 10 µg, about 12.5 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg.

In some exemplary embodiments, the chromatographic column 110 can be capable of being washed with a mobile phase. In one aspect, the mobile phase can be ammonium acetate, ammonium bicarbonate, or ammonium formate, or combinations thereof. In one aspect, the total concentration of the mobile phase that can be used with the chromatographic column 110 can range up to about 600 mM. In a specific aspect, the total concentration of the mobile phase that can be used with the chromatographic column 110 can be about 5 mM, about 6 mM, 7 mM, about 8 mM, 9 mM, about 10 mM, 12.5 mM, about 15 mM, 17.5 mM, about 20 mM, 25 mM, about 30 mM, 35 mM, about 40 mM, 45 mM, about 50 mM, 55 mM, about 60 mM, 65 mM, about 70 mM, 75 mM, about 80 mM, 75 mM, about 95 mM, 100 mM, about 1100 mM, 120 mM, about 130 mM, 140 mM, about 150 mM, 160 mM, about 170 mM, 180 mM, about 190 mM, 200 mM, about 225 mM, 250 mM, about 275 mM, 300 mM, about 325 mM, 350 mM, about 375 mM, 400 mM, about 425 mM, 450 mM, about 475 mM, 500 mM, about 525 mM, 550 mM, about 575 mM, or about 600 mM. In another aspect, the mobile phase that can be used with the chromatographic column 110 can have a flow rate of 0.1 ml/min to 0.4 ml/min. In a specific aspect, the flow rate of the mobile phase that can be used with the chromatographic column 110 can be about 0.1 ml/min, about 0.15 ml/min, about 0.20 ml/min, about 0.25 ml/min, about 0.30 ml/min, about 0.35 ml/min, or about 0.4 ml/min. In another aspect, the mobile phase that can be used with the chromatographic column 110 can be used to elute the impurity.

In some exemplary embodiments, the chromatographic column 110 can be capable of being coupled with a mass spectrometer 120. In one aspect, the mass spectrometer 120 can comprise a nano-spray.

In some exemplary embodiments, the mass spectrometer 120 can be a tandem mass spectrometer.

In some exemplary embodiments, the mass spectrometer 120 can be a native mass spectrometer.

In some exemplary embodiments, the mixed-mode chromatographic system can be capable of detection 140 and/or quantification 130 of a target protein (See FIG. 4). In one aspect, the mixed-mode chromatographic system can be used for detection 140 and/or quantification 130 of one target protein.

In some exemplary embodiments, the mixed-mode chromatographic system can be capable of detection 140 and/or quantification 130 of a monoclonal antibody.

In some exemplary embodiments, the mixed-mode chromatographic system can be capable of detection 140 and/or quantification 130 of a therapeutic antibody.

In some exemplary embodiments, the mixed-mode chromatographic system can be capable of detection 140 and/or quantification 130 of an immunoglobulin protein. In one aspect, the mixed-mode chromatographic system can be capable of detection 140 and/or quantification 130 of an IgG1 protein. In another aspect, the mixed-mode chromatographic system can be capable of detection 140 and/or quantification 130 of an IgG4 protein. In another aspect, the mixed-mode chromatographic system can capable of detection 140 and/or quantification 130 of a bispecific antibody. In yet another aspect, the mixed-mode chromatographic system can capable of detection 140 and/or quantification 130 of an Anti-CD20/CD3 monoclonal antibody.

In some exemplary embodiments, the mixed-mode chromatographic system can be capable of detection 140 and/or quantification 130 of an antibody fragment formed on digestion of the antibody. In one aspect, the mixed-mode chromatographic system can be capable of detection 140 and/or quantification 130 of a target protein, which can be a post-translationally modified protein. In another aspect, the mixed-mode chromatographic system can be capable of detection 140 and/or quantification 130 of a target protein, which can be a degradation product of a protein. In yet another aspect, the mixed-mode chromatographic system can be capable of detection 140 and/or quantification 130 of a target protein which can be an impurity found in a biopharmaceutical product. In another aspect, the mixed-mode chromatographic system can be capable of detection 140 and/or quantification 130 of a target protein which can be an impurity found during the manufacture of the biopharmaceutical product.

In some exemplary embodiments, the mixed-mode chromatographic system can be capable of detection 140 and/or quantification 130 of a target protein which can be a protein with a pI in the range of about 4.5 to about 9.0.

In some exemplary embodiments, the mixed-mode chromatographic system can be capable of detection 140 and/or quantification 130 of a target protein which can be a product-related impurity. The product related impurity can be molecular variants, precursors, degradation products, fragmented protein, digested product, aggregates, post-translational modification form, or combinations thereof.

In some specific exemplary embodiments, the mixed-mode chromatographic system can be capable of detection 140 and/or quantification 130 of a target protein which can be a process-related impurity. The process-related impurity can include impurities derived from the manufacturing process, i.e., nucleic acids and host cell proteins, antibiotics, serum, other media components, enzymes, chemical and biochemical processing reagents, inorganic salts, solvents, carriers, ligands, and other leachables used in the manufacturing process. In one aspect, the number of impurities in the sample can be at least two.

In some exemplary embodiments, the chromatographic column 110 capable of being used for at least about 3 sample runs without cleaning. In one aspect, the chromatographic column 110 can be used for at least about 3 sample runs, at least about 4 sample runs, at least about 5 sample runs, at least about 6 sample runs, at least about 7 sample runs, or at least about 8 sample runs, without cleaning.

It is understood that the system is not limited to any of the aforesaid protein, impurity, mobile phase, or chromatographic column.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is incorporated by reference, in its entirety and for all purposes, herein.

The disclosure will be more fully understood by reference to the following Examples, which are provided to describe the disclosure in greater detail. They are intended to illustrate and should not be construed as limiting the scope of the disclosure.

EXAMPLES

Materials. Deionized water was provided by a Milli-Q integral water purification system installed with MilliPak Express 20 filter (MilliporeSigma, Burlington, Mass.). Ammonium acetate (LC/MS grade), acetic acid and ammonium bicarbonate (LC/MS grade) were purchased from Sigma-Aldrich (St. Louis, Mo.). Peptide N-glycosidase F (PNGase F) was purchased from New England Biolabs Inc (Ipswich, Mass.). Invitrogen™ UltraPure™ 1 M Tris-HCl buffer, pH 7.5 was obtained from Thermo Fisher Scientific (Waltham, Mass.). All monoclonal antibodies and bispecifics, including IgG1 and IgG4 subclasses were produced at Regeneron.

Sample Preparation. To reduce the mass heterogeneity introduced by the presence of two N-linked glycans in the Fc portion, each antibody or antibody mixture sample was treated with PNGase F (1 IUB milliunit per 10 μg of protein) at 45° C. in 100 mM Tris-HCl (pH 7.5) for 1 hour. To prepare the spike-in standards of bsAb mixtures, the bsAb drug substance was first further purified using analytical strong cation exchange chromatography (SCX) to remove any residual homodimer impurities from the large-scale manufacturing process. The detailed conditions for SCX fractionation are shown below. After fractionation, both the purified BsAb and the corresponding homodimer standards were buffer exchanged into 50 mM of Tris-HCl buffer (pH 7.5) and each adjusted to 6 μg/μL based on concentrations determined by Nanodrop (Thermo Fisher Scientific, Bremen, Germany). Subsequently, the bsAb and the two corresponding homodimers were mixed at a ratio of 1:1:1. Finally, sequential dilutions were performed using a 2 μg/μL bsAb solution to prepare a series of spike-in standards with the homodimer levels ranging from 0.1% to 10%.

Purification of bsAb from the bsAb drug substance by SCX. For further purification of the bsAb from each bsAb sample, analytical strong cation exchange chromatography (SCX) was performed on a Waters I-Class UPLC system equipped with photodiode array (PDA) detector (Waters, Milford, Mass., US). Prior to sample injection, the column compartment temperature was set at 45° C. and a YMC-BioPro SP-F strong cation exchange column (100 mm×4.6 mm, 5 μm) (YMC Co., LTD., Kyoto, Japan) was preconditioned with mobile phase A (20 mM ammonium acetate, pH adjusted to 5.6 with 20 mM acetic acid) at a flow rate of 0.4 mL/min. Upon the injection of an aliquot (200 μg) of the protein samples, the gradient is held at 100% mobile phase A for 2 minutes followed by a linear increase to 100% mobile phase B (140 mM ammonium acetate, 10 mM ammonium bicarbonate, pH 7.4) in 16 minutes. The gradient was held at 100% mobile phase B for 4 minutes and then returned to 100% mobile phase A to recondition the column for 7 minutes before the next injection. The fractionated BsAb was then buffer exchanged into the same buffer as the mispaired homodimer samples before mixing to prepare the spike-in standards.

MM-SEC-MS Method. Mixed-mode size exclusion chromatography was performed on a Waters I-Class UPLC system equipped with photodiode array (PDA) detector (Waters, Milford, Mass., US). A Thermo Exactive Plus EMR mass spectrometer equipped with a Nanospray Flex™ Ion Source (Thermo Fisher Scientific, Bremen, Germany) was used for mass measurement. Prior to sample injection, the column (Waters BEH200 SEC 4.6×300 mm, 200 Å, 1.7 μm or Sepax Zenix SEC-300 4.6×300 mm, 300 Å, 3 μm) was pre-equilibrated at a flow rate of 0.2 mL/min using ammonium acetate- and ammonium bicarbonate-based mobile phase of varying concentrations (30 mM to 450 mM). This was achieved by running at a fixed percentage of mobile phase B using a dual solvent system (mobile phase A: water; mobile phase B: 420 mM ammonium acetate and 30 mM ammonium bicarbonate). Upon injection of an antibody sample (2-10 μg), an isocratic elution method was run for 24 minutes. To enable simultaneous UV and MS detection, a post-column splitter (~200:1 ratio) was applied after the SEC separation to reduce the flow to ~1 μL/min for nano-ESI-MS analysis, while diverting the remaining high flow to the PDA detector for UV monitoring at 280 nm. A disposable PicoTip Emitter (non-coated, tip: 10±1 μm) (New Objective, Inc., Woburn, Mass., US) was used to achieve nano-ESI. For the mass spectrometric analysis, the resolution was set at 17,500, the capillary spray voltage was set at 1.5 kV, the in-source fragmentation energy was set at 100, the collision energy was set at 10, the capillary temperature was set at 350° C., the S-lens RF level was set at 200 and the HCD trapping gas pressure was set at 3. Mass spectra were acquired with an m/z range window between 2000 and 15000.

Example 1. Secondary Interactions During SEC Using MS-Compatible Buffer

A protein surface is highly heterogeneous and consists of many different functional groups that can contribute to hydrogen bonding (hydroxyl, amine and amide groups), electrostatic (charged groups), and hydrophobic (hydrophobic groups) interactions with the silica- or polysaccharide-based SEC column matrix. These interactions, in general, have different binding strength and are highly dependent on the pH, temperature and mobile phase composition used in the SEC application. For example, when performed at near neutral pH, the silanol groups from a silica-based SEC column can be negatively charged, and therefore promote an electrostatic interaction with basic proteins. To suppress such an interaction, mobile phases with moderate ionic strength (Goyon et al, 2018, supra) or low pH (less than 5) (Pavon et al, 2016, supra) were frequently required in the past.

More recently, via silica surface derivatization (such as short alkyl chains or linkage of functional groups), the residual silanol groups from a modern SEC column can be effectively shielded, and therefore, dramatically reduce the presence of electrostatic interactions. However, those newly introduced chemical groups might also result in other enhanced secondary interactions (e.g., hydrophobic interaction) with the protein analyte, as reported in recent studies (Yang et al, 2015, supra; Van He et al., *On-line coupling of size exclusion chromatography with mixed-mode liquid chromatography for comprehensive profiling of biopharmaceutical drug product*, 1262 JOURNAL OF CHROMATOGRAPHY A 122-129 (2012)). As summarized by Arakawa et al., electrostatic interactions dominate at low salt concentrations, whereas hydrophobic interactions are favored with high ionic strength mobile phases, particularly when higher-ranking salts in the Hofmeister series (See FIG. 3) are used. Although the choice of salts compatible with online SEC-MS application is generally limited (e.g., ammonium formate, ammonium acetate and ammonium bicarbonate), different types of secondary interactions between the protein analytes and the column matrix might still be modulated by varying salt concentrations and explored for protein separation purposes.

Figure 5:
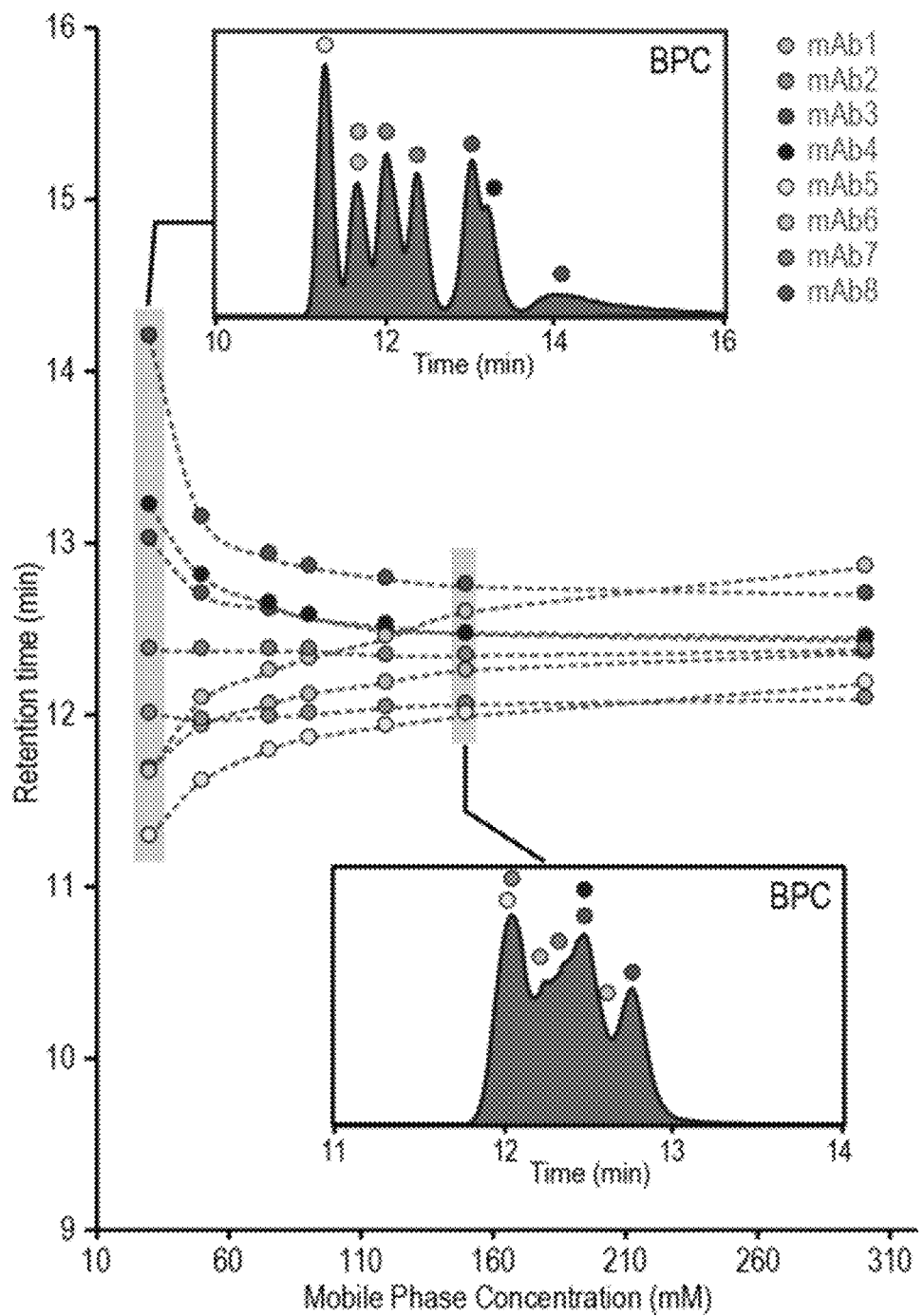
FIG. 5 shows the plots of the retention time of eight mAbs in the sample mixture on the BEH200 SEC column performed under mobile phase concentrations ranging from 30 mM to 300 mM, wherein the two insets represent the base peak chromatograms (BPCs) from the MM-SEC-MS analysis of the eight mAbs at the corresponding concentrations according to an exemplary embodiment.

To assess the mixed-mode interactions associated with salt concentration, a mixture of eight antibodies (both IgG1 and IgG4 subclasses) with different surface characteristics were analyzed on a Waters BEH200 SEC column using ammonium acetate- and ammonium bicarbonate-based mobile phases of varying concentrations from 30 mM to 300 mM, a range that is feasible for subsequent native MS analysis. The molar ratio between ammonium acetate and ammonium bicarbonate was kept constant at 14:1 to achieve a pH value of approximately 7.4. The chromatographic behavior of the eight mAbs were illustrated by plotting their SEC retention times, as determined by extracted ion chromatograms (XICs), against the mobile phase concentration (FIG. 5). Overall, the eight mAbs were most well separated when SEC was performed using a mobile phase salt concentration of 30 mM. As the salt concentration increased, the elution profiles of the eight mAbs became more converged and less resolved (insets in FIG. 5). These shifts in retention times could be explained by the changes in secondary interactions between the mAb molecule and the column matrix. On one hand, as the residual silanol groups from the column matrix became negatively charged at pH 7.4, they could interact with the positively charged protein surface via electrostatic interaction. This interaction gets enhanced when lower salt concentration is used. On the other hand, hydrophobic interaction between the mAb molecule and the column matrix could be promoted when higher salt concentrations are used. Interestingly, based on their pI values, these eight mAbs can be categorized into three different groups, where similar relationships between the retention time and salt concentration were observed. The first group includes the three acidic mAb molecules, mAb5 (pI=6.3), mAb6 (pI 6.4) and mAb1 (pI=6.7), which are expected to bear fewer positive charges on the protein surface at pH 7.4, and therefore exhibited the least electrostatic interactions with the column matrix. As shown in FIG. 5, these three molecules all showed an increasing trend of retention time as the salt concentration increased, indicating that as weak electrostatic interactions are eliminated at higher ionic strength, the hydrophobic interaction plays a dominant role during the SEC separation. On the contrary, the three basic mAb molecules, mAb3 (pI=8.0), mAb4 (pI=8.3) and mAb8 (pI=7.6), which are expected to bear more positive charges on the protein surface at pH 7.4, all showed a decreasing trend in retention time as the salt concentration increased. This inverse correlation between the salt concentration and retention time was mainly attributed to the dominating electrostatic interaction, which was promoted at low salt concentration and suppressed at high salt concentration. Lastly, unlike either the acidic or basic mAbs, mAb2 (pI=7.3) and mAb7 (pI=6.9) represent a "neutral" group, which likely bear a moderate amount of positive charges on the protein surface, and therefore exhibited a medium level of electrostatic interactions with the column matrix. This group of molecules maintained a relatively unchanged retention time at varying salt concentrations (30 mM to 300 mM). In this case, as the salt concentration increased, the increase in hydrophobic interaction was likely close to and counteracting the decrease in electrostatic interaction, leading to little shift in retention time. These results indicated that by properly modulating the salt concentrations, it might be possible to separate or partially separate different antibodies (e.g., bsAb vs. homodimers) using mixed-mode interactions on a SEC column for subsequent MS analysis.

Although it appears that greater chromatographic resolution was achieved at low salt concentrations on a Waters BEH column, caution needs to be taken for basic mAbs, as severe peak tailing may occur under those conditions and could significantly impact the protein recovery (Alexandre Goyon et al., *Characterization of 30 therapeutic antibodies and related products by size exclusion chromatography: Feasibility assessment for future mass spectrometry, hyphenation*, 1065-1066 JOURNAL OF CHROMATOGRAPHY B 35-43 (2017)).

Example 2. Detection of O-Glycan Variant of a Bispecific Antibody Bispecific Ab Using MM-SEC-MS 2.1 Sample Preparation of Bispecific Antibody The anti-CD20×anti-CD3 Bispecific Antibody (BsAb1) is a hinge-stabilized CD20×CD3 bispecific full-length antibody (Ab) based on an IgG4 isotype modified to reduce Fc binding. It is designed to bind T cells (via CD3) and CD20-expressing cells. The Bispecific Antibody was produced by following the methodology as described by Smith et al. (Sci. Rep. (2015) 5:17943).

2.2 MINI-SEC-MS

The analysis using MM-SEC-MS was performed isocratically using a Zenix SEC-300 MK column (7.8×300 nm, 3 µm) on the system as described above. Elution was monitored by UV at 280 nm.

Two sets of experiments were carried out. In the first experiment, the mobile phase comprised 140 mM ammonium acetate and 10 mM ammonium bicarbonate and in the second experiment, the mobile phase comprised 420 mM ammonium acetate and 30 mM ammonium bicarbonate. The elution was carried out at a flow rate of 0.4 mL/min. The equilibration was performed using the mobile phase.

For analytical runs, the injection loads consisted of 100 µg of the total protein. The elution was carried out using an isocratic gradient consisting of ammonium acetate (buffer A) and ammonium bicarbonate (buffer B). The mass spectrometry data was analyzed by using Intact software from Protein Metrics.

Figure 6:
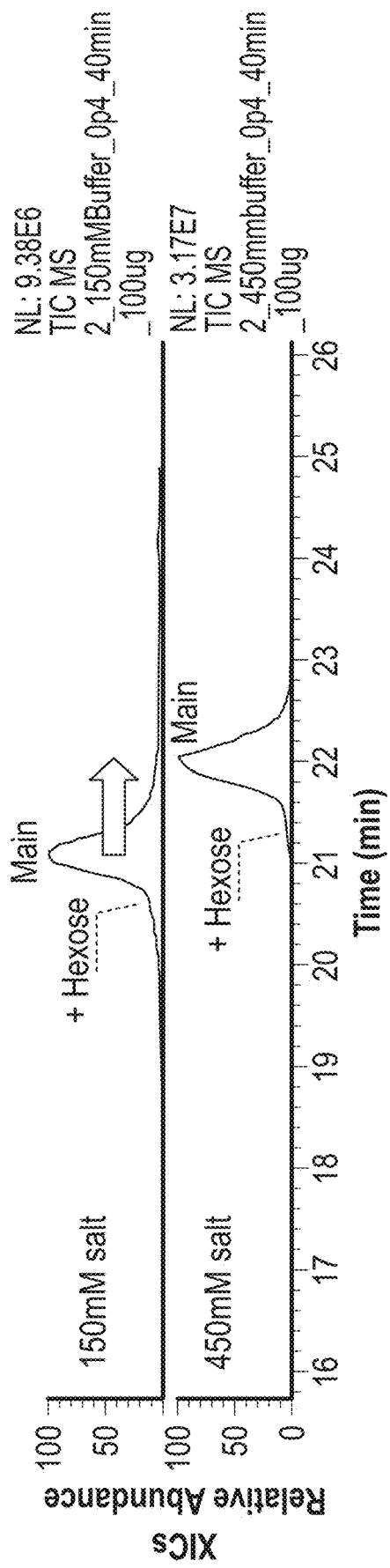
FIG. 6 shows the chromatographic profile of the bispecific antibody mixed-mode size chromatography sample using an exemplary mass spectrometry system using mobile phases: 150 mM total salt concentration and 450 mM total salt concentration.
Figure 6:
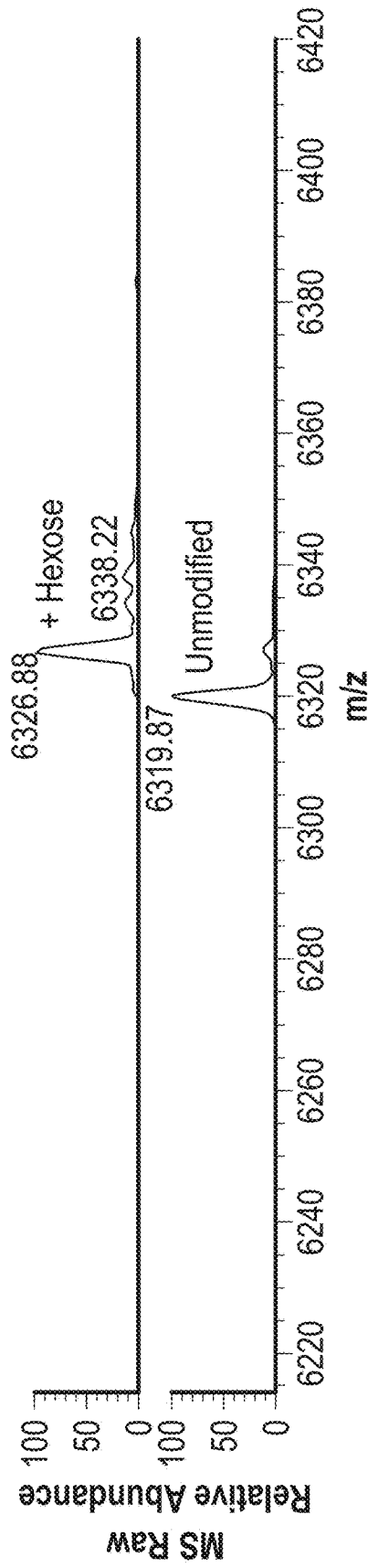

The two runs with mobile phases of differing concentration revealed that higher salt concentration can enhance the hydrophobic interaction during SEC separation as observed from elution time of the bispecific antibody in different mobile phases. This effect led to an increased separation between the bispecific antibody and its O-glycan variant (See FIG. 6).

Example 3. Detection of Homodimer Species Using Zenix SEC-300, 3 µm, 300 Å, 7.8×300 mm 3.1 Sample Preparation of Bispecific Antibody and Homodimers Mixture Standards Two homodimer impurities are generated during the production of the bispecific antibody (BsAb1) (Fc*/Fc): homodimer 1 (Fc*-Fc*) and homodimer 2 (Fc/Fc) (See FIG. 2).

3.2 MINI-SEC-MS

The acquisition using MM-SEC-MS was performed isocratically using a Zenix SEC-300 MK column (7.8×300 nm, 3 µm) on the system as described above. Elution was monitored by UV at 280 nm.

Two set of experiments were carried out. In the first experiment, the mobile phase comprised 140 mM ammonium acetate and 10 mM ammonium bicarbonate and in the second experiment, the mobile phase comprised 420 mM ammonium acetate and 30 mM ammonium bicarbonate. The elution was carried out at a flow rate of 0.4 mL/min.

Figure 7:
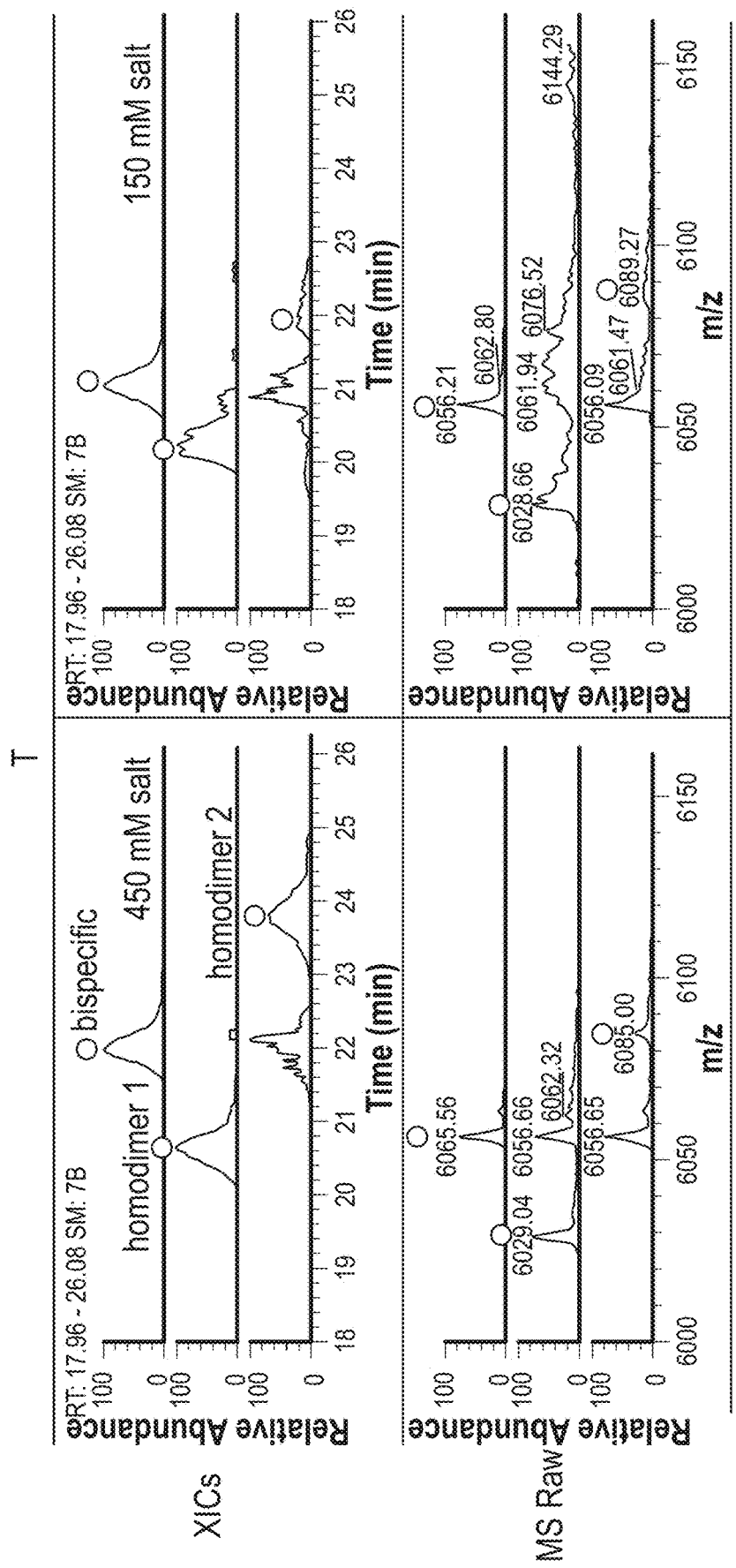
FIG. 7 shows the extracted ion chromatogram (XIC) and the native mass spectra of the bispecific antibody, homodimer 1 and homodimer 2 separated and analyzed using a mixed-mode size exclusion chromatography mass spectrometry according to an exemplary embodiment.

For analytical runs, the injection loads consisted of 50 µg of the total protein. The elution was carried out using an isocratic gradient consisting of ammonium acetate (buffer A) and ammonium bicarbonate (buffer B). Similar to results obtained form 2.2, the two runs with mobile phases of differing concentration revealed that higher salt concentration can enhance the hydrophobic interaction during SEC separation as observed from the elution times of the bispecific antibody and the homodimers in the different mobile phases. The mobile phase with total salt concentration of 450 mM performed an improved separation of the homodimer 1 and homodimer 2 from the bispecific antibody (See FIG. 7).

Example 4. Comparison of the Detection of Homodimer Impurities in the Bispecific Antibody Using MM-SEC-MS, SEC-MS and RP LC-MS 4.1 Sample Preparation of Bispecific Antibody and Homodimers Mixture Standards The sample was prepared using the methodology illustrated in example 3.

4.2 RP LC-MS

The sample was diluted to 0.5 mg/mL. This solution was injected at 0.5 μs for LC-MS analysis. The LC-MS experiment was performed on ThermoFisher Fusion Lumos Tribrid mass spectrometer. The Waters BioResolve™ mAb Polyphenyl, 450 Å, 2.7 μm 2.1×50 mm Column (P.N. 186008944) was used for reverse phase separation. The sample temperature was set at 5° C. and column temperature was set at 80° C. The mobile phase A was 0.1% FA in water, mobile phase B was 0.1% FA in acetonitrile. The mass spectrometry experiment was performed in positive mode. The MS ion source conditions were set as the following: spray voltage at 3.8 kV, ion transfer tube temperature at 325° C., vaporizer temperature at 250° C., sheath gas at 40 (Arb), Aux gas at 10 (Arb), sweep gas at 2 (Arb), RF Lens (%) at 60 and source fragmentation energy at 40 V. MS data were acquired by orbitrap in high mass range mode with m/z range at 1500-4000. Resolution was set to 15,000 at m/z 200 with 10 microscans, AGC target was $10^5$, maximum injection time was 50 ms. The mass spectrometry data was analyzed by using Xaclibur software.

4.3 SEC-MS

Size exclusion chromatography (SEC) was performed on the ACQUITY UPLC Protein BEH SEC Column (200 Å, 1.7 μm, 4.6 mm×300 mm) using mobile phase comprised 140 mM ammonium acetate and 10 mM ammonium bicarbonate. The SEC experiments were performed on a Waters Acquity UPLC I-class system at room temperature, with wavelength detection at 280 nm, a 0.2 mL/min flow rate, and 50 μg protein injection load.

4.4 MM-SEC-MS

The analytical run on the MM-SEC-MS system was carried out isocratically using a mobile phase containing 420 mM ammonium acetate and 30 mM ammonium bicarbonate using a methodology illustrated in Example 3.2.

4.5 Results

Figure 8:
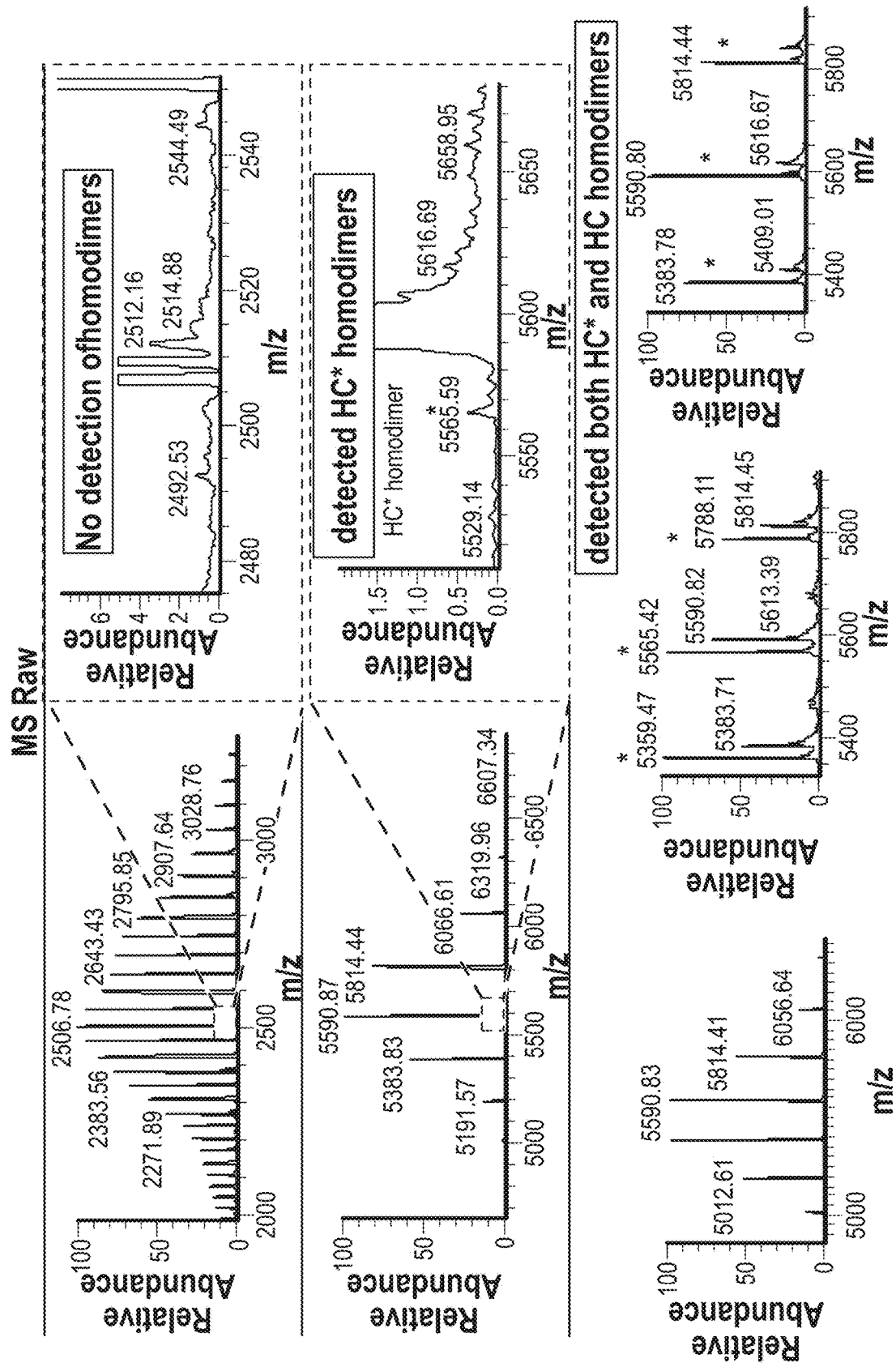
FIG. 8 shows comparison of the total ion chromatogram (TIC) and the native MS spectra for RP LC-MS on Lumos, SEC-MS on EMR, and MM-SEC-MS on EMR of an antibody detected spectrometry according to an exemplary embodiment.
Figure 8:
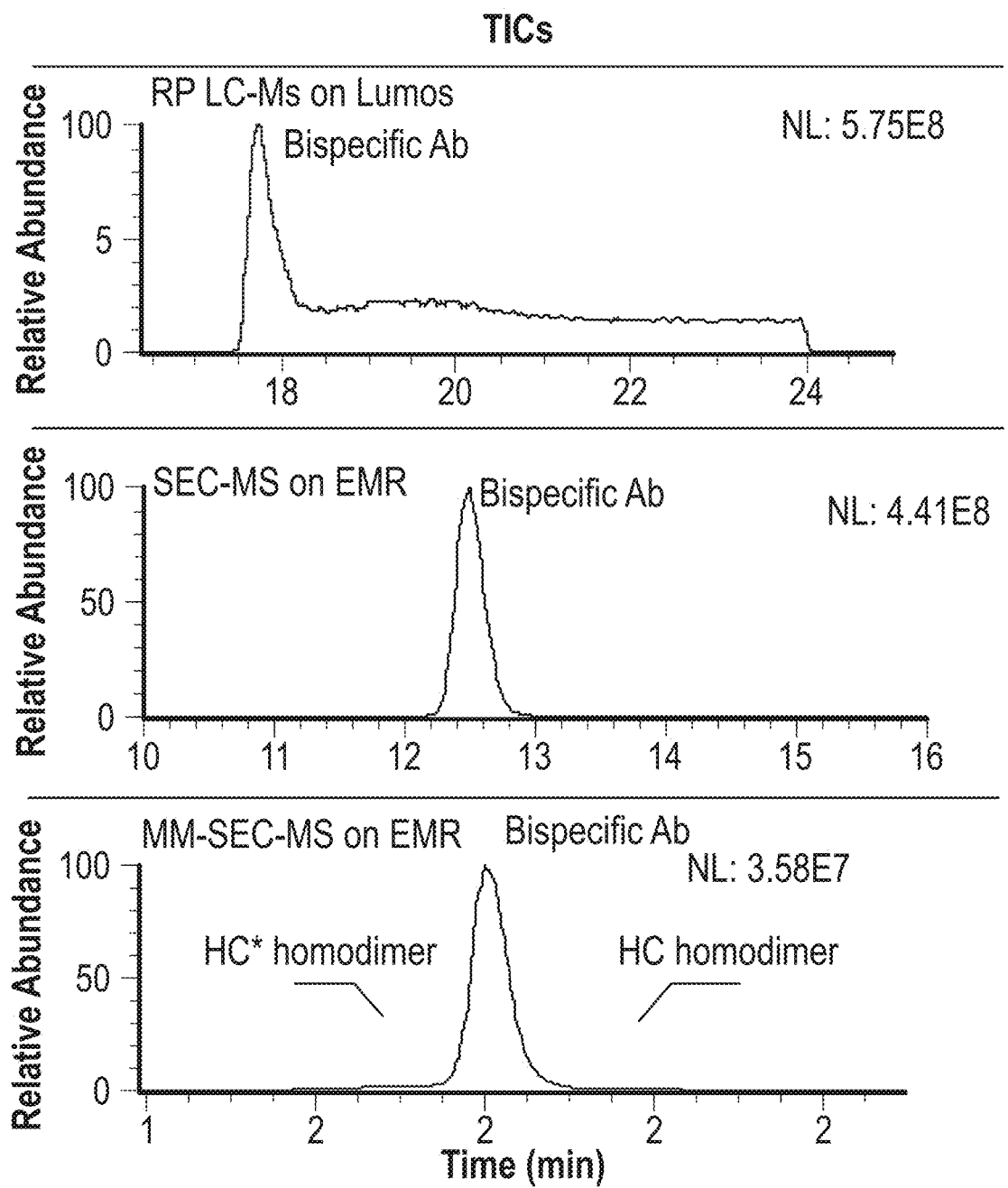

Comparison of the total ion chromatogram (TIC) and the native MS spectra for RP LC-MS on Lumos (See FIG. 8), SEC-MS on EMR, and MM-SEC-MS on EMR shows the significant separation and detection of homodimers from the bispecific antibody. The raw mass spectrogram from RP LC-MS was unable to differentiate between the homodimers and the bispecific antibody. The raw mass spectrum from SEC-MS was able to separate and detect homodimer 1 and the bispecific antibody, but the separation was not sufficient to separate and detect homodimer 2 and the bispecific antibody. Only the raw mass spectra from MM-SEC-MS showed sufficient separation and detection of homodimer 1, homodimer 2 and the bispecific antibody. This comparison provides a proof of concept of superiority of MM-SEC-MS over SEC-MS and RP LC-MS for detection of impurities in biopharmaceutical products.

Example 5. Consecutive Runs of MM-SEC-MS Detection Using Zenix SEC-300, 3 μm, 300 Å, 7.8×300 mm To evaluate the data quality of detection in consecutive runs, three analytical runs of the sample containing Bispecific Ab, homodimer 1, and homodimer 2 (prepared as illustrated in 4.1) was carried out using the MM-SEC-MS system. The analytical runs were performed using the methodology illustrated in 4.2 and mobile phase comprising 280 mM ammonium acetate and 20 mM ammonium bicarbonate.

Figure 9:
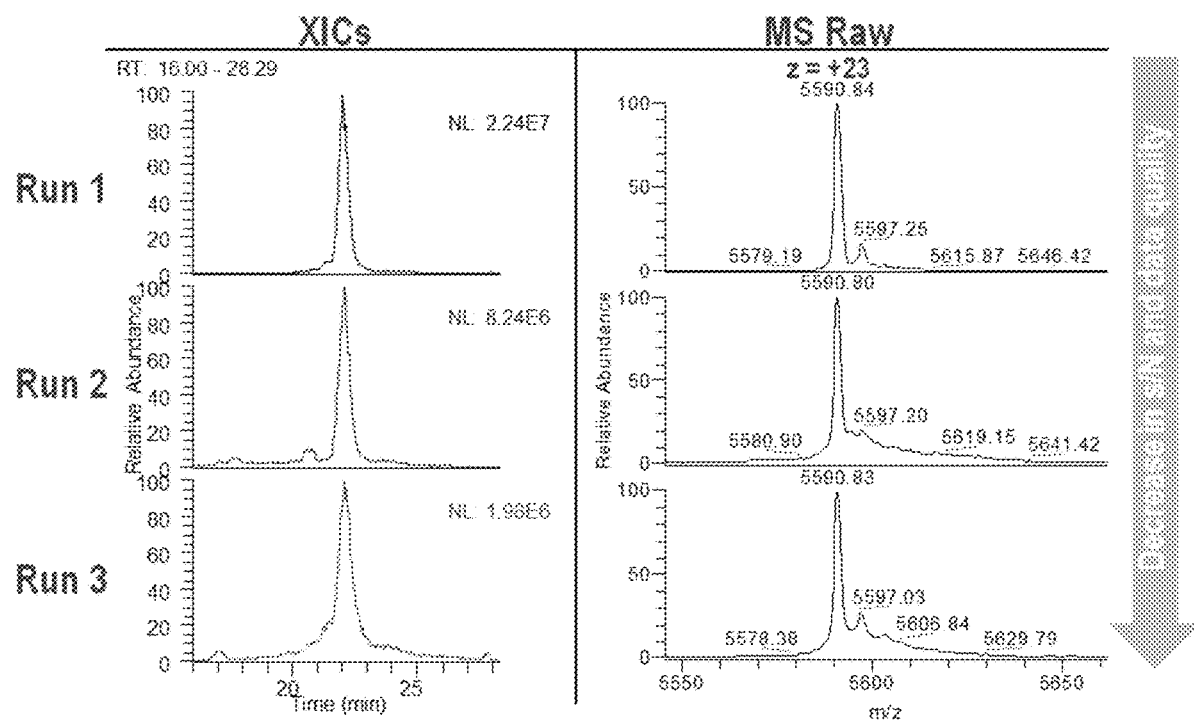
FIG. 9 shows extracted ion chromatograms (XIC) and the native mass spectra of consecutive runs of MM-SEC-MS detection of an antibody using Zenix SEC-300, 3 µm, 300 Å, 7.8×300 mm according to an exemplary embodiment.

The raw mass spectra and the extracted ion chromatogram (XIC) for the three runs showed a decrease in data quality and signal to noise ratio (See FIG. 9). This effect could be because of the use of a large column (7.8×300 mm) which requires a large amount of protein sample (~50 μg) to ensure MS intensity, which can lead to protein precipitation at the high salt concentration and therefore requires more frequent cleaning of the flow pathway (max 3 samples run before cleaning).

Further, the large column and relative low flow rate the nanosplitter can handle (max~0.4 mL/min) led to broad peak width (~1.5 min), which affects the MS intensity and resolution in some cases. The late elution time also slowed down overall analysis time (30 min each sample).

Example 6. Detection of Homodimer Species Using Zenix SEC-300, 3 μm, 300 Å, 4.6×300 mm 6.1 Sample Preparation of Bispecific Antibody and Homodimers Mixture Standards The Bispecific Antibody and homodimers mixture standards can be prepared by methods illustrated in 3.1

6.2 MINI-SEC-MS

The acquisition using MM-SEC-MS was performed isocratically using a Zenix SEC-300 MK column (4.6×300 nm, 3 μm) on the system as described above. Elution was monitored by UV at 280 nm.

Four set of experiments were carried out. In the first experiment, the mobile phase comprised 140 mM ammonium acetate and 10 mM ammonium bicarbonate, in the second experiment, the mobile phase comprised 280 mM ammonium acetate and 20 mM ammonium bicarbonate, in the third experiment, the mobile phase comprised 420 mM ammonium acetate and 30 mM ammonium bicarbonate and in the second experiment, the mobile phase comprised 560 mM ammonium acetate and 40 mM ammonium bicarbonate. The elution was carried out at a flow rate of 0.3 mL/min.

Figure 10:
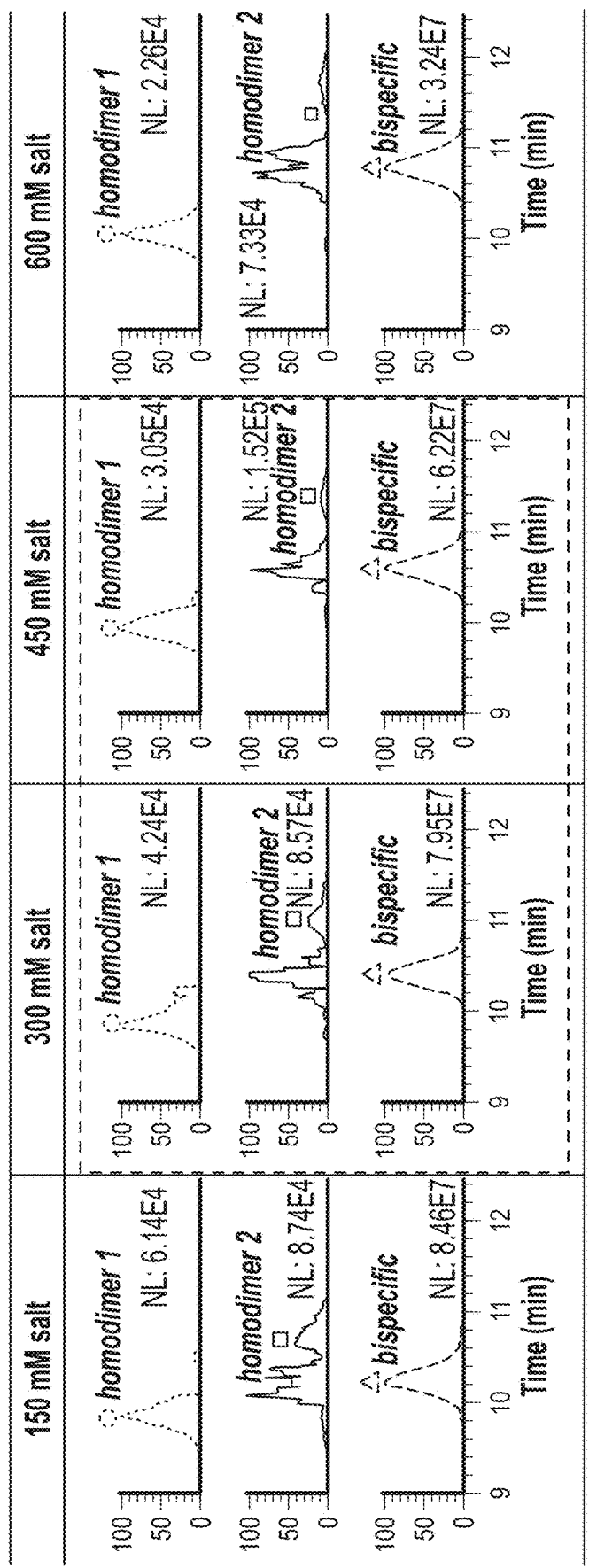
FIG. 10 shows extracted ion chromatograms (XIC) obtained on performing detection of homodimer species in a bispecific antibody product according to an exemplary embodiment.
Figure 11:
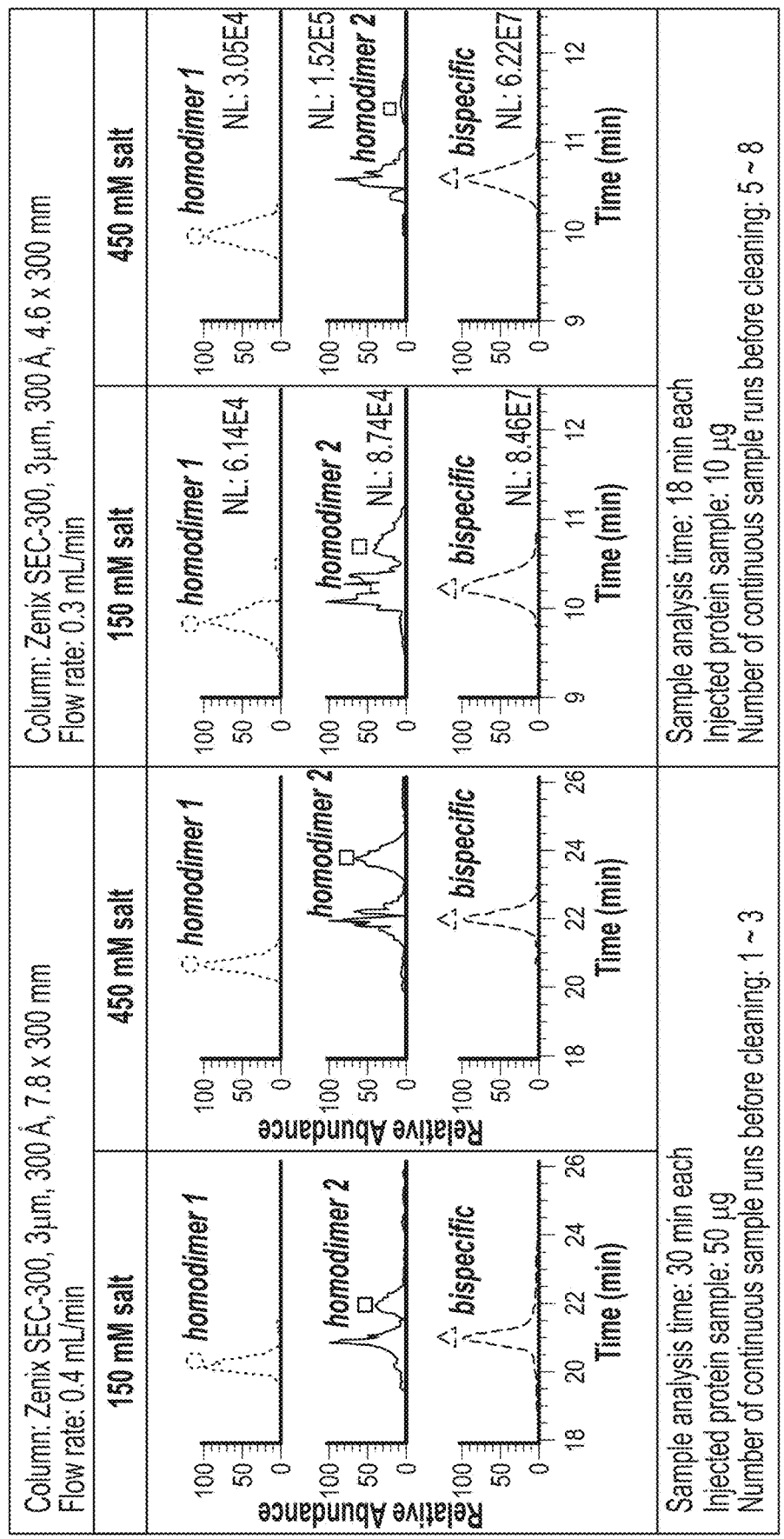
FIG. 11 shows comparison of the extracted ion chromatograms (XIC) obtained on performing detection of homodimer species in a bispecific antibody product using a Zenix SEC-300, 3 µm, 300 Å, 7.8×300 mm at 0.4 mL/min flow rate and Zenix SEC-300, 3 µm, 300 Å, 4.6×300 mm at 0.3 mL/min flow rate according to an exemplary embodiment.

For analytical runs, the injection loads consisted of 10 μg of the protein. The elution was carried out using an isocratic gradient consisting of ammonium acetate (buffer A) and ammonium bicarbonate (buffer B). The use of concentrations greater than 150 mM total salt concentration shows an improved separation and detection of the homodimers and bispecific antibody (See FIG. 10). The total time for analysis on using the smaller column (4.6×300 nm) decreased to about 18 minutes and the peak width decrease to less than 1 minute, compared to the total time for analysis and peak width on using the larger column (7.8×300 nm). Representations of the differences are shown in FIG. 11.

Example 7. MM-SEC-MS Analysis of Deglycoslyated Mixture of Bispecific Antibody, Homodimer 1, and Homodimer 2 on Zenix-SEC Column 7.1 Preparation of Deglycoslyated Mixture of Bispecific Antibody, Homodimer 1, and Homodimer 2

Each protein was treated with peptide N-glycosidase F (PNGase F; 1 IUB milliunit per 10 μg of protein) at 45° C. for 1 hour to completely remove the glycan chains from each heavy chain constant region.

7.2 MINI-SEC-MS

The acquisition using MM-SEC-MS was performed isocratically using a Zenix SEC-300 MK column (4.6×300 nm, 3 µm) on the system as described above. Elution was monitored by UV at 280 nm.

Six set of experiments were carried out. In the first experiment, the mobile phase comprised 9.3 mM ammonium acetate and 0.7 mM ammonium bicarbonate, in the second experiment, the mobile phase comprised 46.7 mM ammonium acetate and 3.3 mM ammonium bicarbonate, in the third experiment, the mobile phase comprised 93.3 mM ammonium acetate and 6.7 mM ammonium bicarbonate, in the fourth experiment, the mobile phase comprised 186.7 mM ammonium acetate and 13.3 mM ammonium bicarbonate, in the fifth experiment, the mobile phase comprised 280 mM ammonium acetate and 20 mM ammonium bicarbonate, and in the sixth experiment, the mobile phase comprised 420 mM ammonium acetate and 30 mM ammonium bicarbonate. The elution was carried out at a flow rate of 0.3 mL/min.

For analytical runs, the injection loads consisted of 10 µg of the protein.

Figure 12:
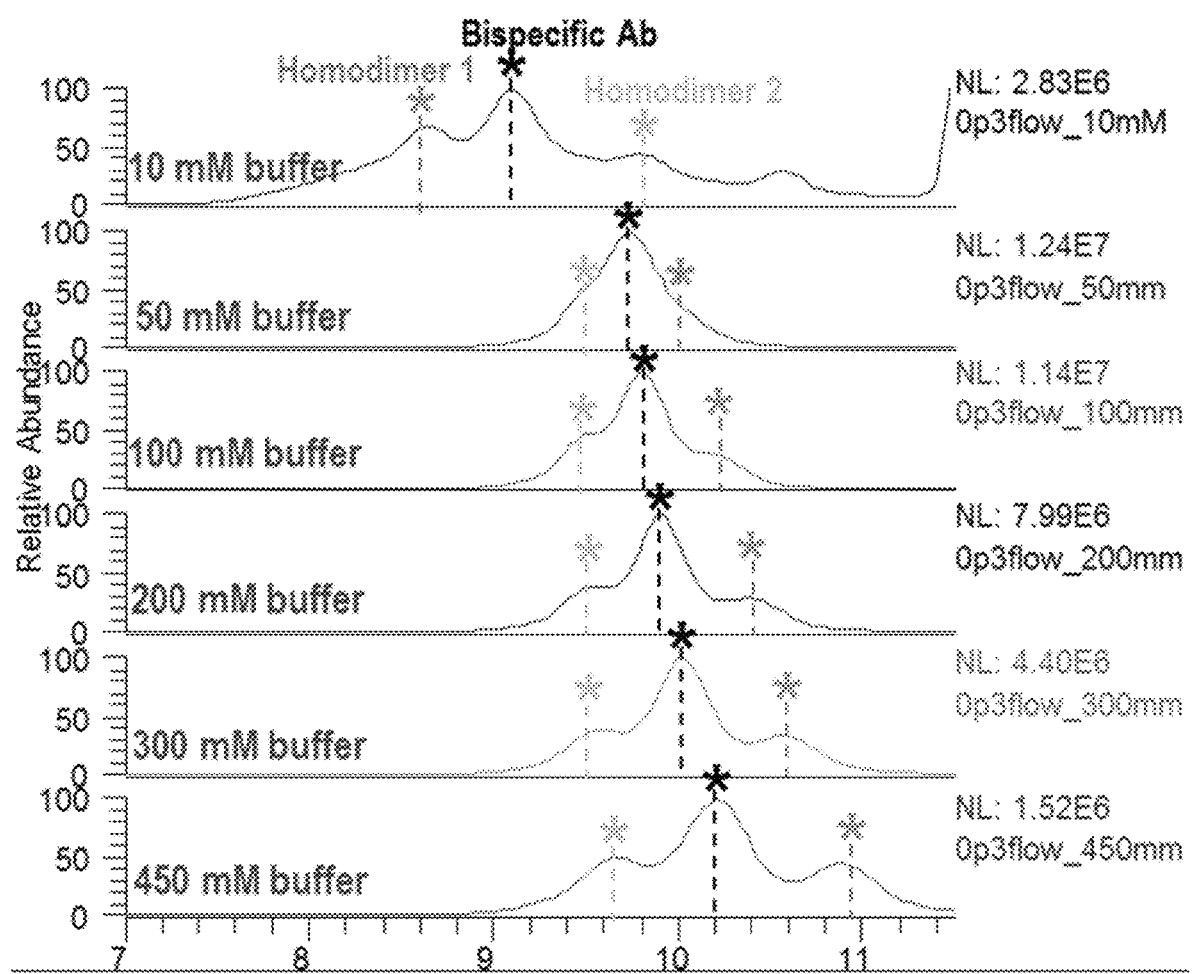
FIG. 12 shows the extracted ion chromatograms (XIC) obtained on performing MM-SEC-MS analysis of deglycosylated mixture of bispecific antibody, homodimer 1, and homodimer 2 using mobile phase with different salt concentration according to an exemplary embodiment.
Figure 13:
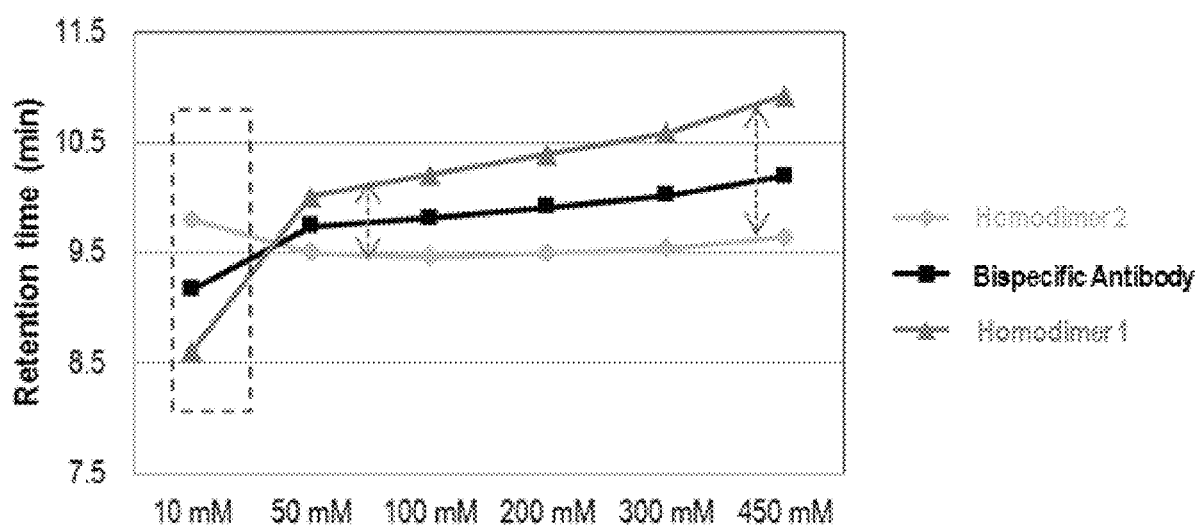
FIG. 13 shows the chart of retention time (minute) of a protein vs. total salt concentration of the mobile phase for a deglycosylated mixture of bispecific antibody, homodimer 1, and homodimer 2 on performing MM-SEC-MS analysis according to an exemplary embodiment.
Figure 14:
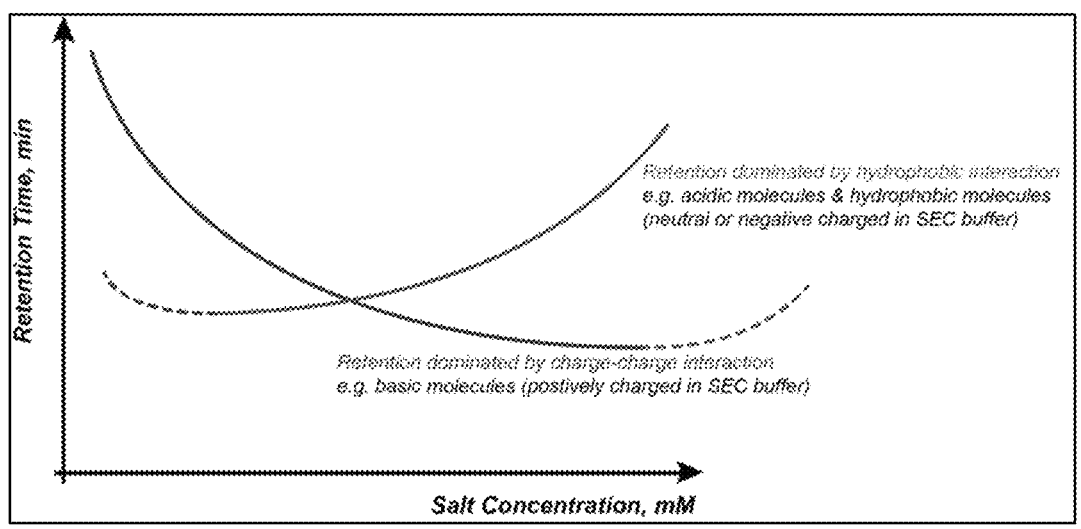
FIG. 14 represents a chart showing trend in retention time based on changing total salt concentration on performing MM-SEC-MS analysis according to an exemplary embodiment.
Figure 15:
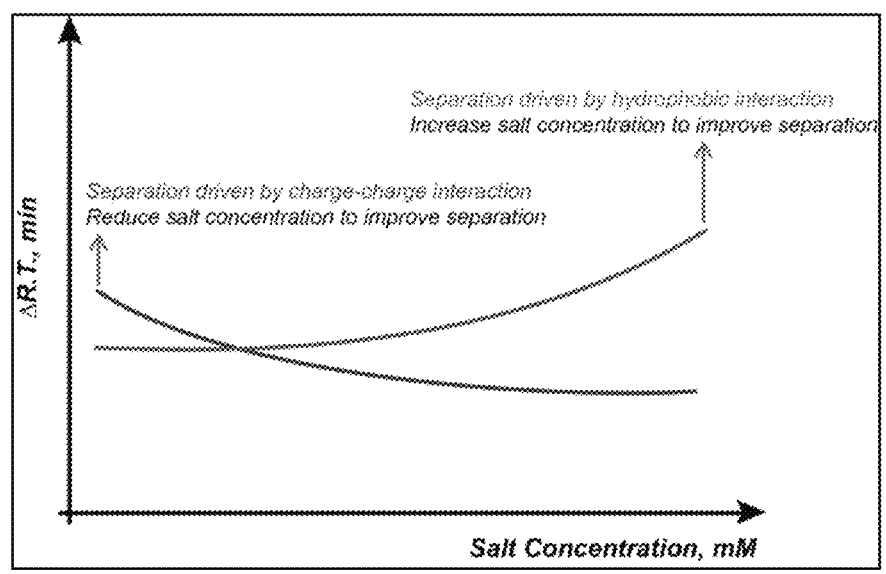
FIG. 15 represents a chart showing a trend in difference in retention time on changing total salt concentration on performing MM-SEC-MS analysis according to an exemplary embodiment.

The use of 10 mM total salt concentration shows significant separation of the homodimer 1, bispecific antibody, and homodimer 2. At 10 mM salt concentration, homodimer 2 had a later retention time than the bispecific antibody, which showed a later retention time than homodimer 1. However, at concentrations greater than 10 mM, homodimer 1 had a later retention time than the bispecific antibody, which showed a lower retention time than homodimer 2 (See FIG. 12 and FIG. 13). This effect could be due to different type of interaction: charge, shape, or hydrophobicity of the three proteins with the size exclusion chromatography resin used. The charge on the protein at a given salt concentration depends on their pI values (Table 2). Significant separations were obtained either by using mobile phase with low salt concentration of 10 mM or by using mobile phase with high salt concentration greater than 100 mM. At lower salt concentrations, retention can be driven by charge-charge interaction. For example, basic molecules can be separated by using mobile phase with lower salt concentration, in the MM-SEC-MS system. At higher salt concentrations, retention is driven by hydrophobic interaction. For example, acidic or hydrophobic molecules can be separated by using mobile phase with higher salt concentration, in the MM-SEC-MS system (See FIG. 14 and FIG. 15).

An ideal SEC separation should be only based on hydrodynamic volume of the protein, and no other interaction should be desired between the protein and the stationary phase. Since, silica-based column matrix might exhibit negative charges due to silanol groups (ion-exchange characteristics), derivatization of the silica particle helps to reduce the silanol effect but and the same time might introduce new interaction mechanism (hydrophobicity). This can thus create SEC resins which have functionality, as observed with the Zenix SEC-columns. This explains the difference in the order of elution of the proteins with different concentrations when carried out in a Zenix-SEC column.

TABLE 2

| mAb | pI | MW |
| --- | --- | --- |
| Bispecific Antibody | 7.66 | 145,337 |
| Homodimer 1 (Bispecific Antibody HC* homodimer) | 8.03 | 144,677 |
| Homodimer 2 (Bispecific Antibody HC homodimer) | 7.28 | 145,998 |

Example 8. MM-SEC-MS Analysis of Deglycoslyated Mixture of Bispecific Antibody, Homodimer 1, and Homodimer 2 on Waters BEH SEC Column 8.1 Preparation of deglycoslyated mixture of bispecific antibody, homodimer 1, and homodimer 2.

The deglycosylated mixture was prepared using the same methodology as 7.1

8.2 MINI-SEC-MS

The acquisition using MM-SEC-MS was performed isocratically using a Waters BEH SEC Colum on the system as described above. Elution was monitored by UV at 280 nm.

Six set of experiments were carried out. In the first experiment, the mobile phase comprised 14 mM ammonium acetate and 1 mM ammonium bicarbonate, in the second experiment, the mobile phase comprised 18.7 mM ammonium acetate and 1.3 mM ammonium bicarbonate, in the third experiment, the mobile phase comprised 28 mM ammonium acetate and 2 mM ammonium bicarbonate, in the fourth experiment, the mobile phase comprised 70 mM ammonium acetate and 5 mM ammonium bicarbonate, in the fifth experiment, the mobile phase comprised 93.3 mM ammonium acetate and 6.7 mM ammonium bicarbonate, and in the sixth experiment, the mobile phase comprised 280 mM ammonium acetate and 20 mM ammonium bicarbonate. The elution was carried out at a flow rate of 0.2 mL/min.

For analytical runs, the injection loads consisted of 10 µg of the protein.

Figure 16:
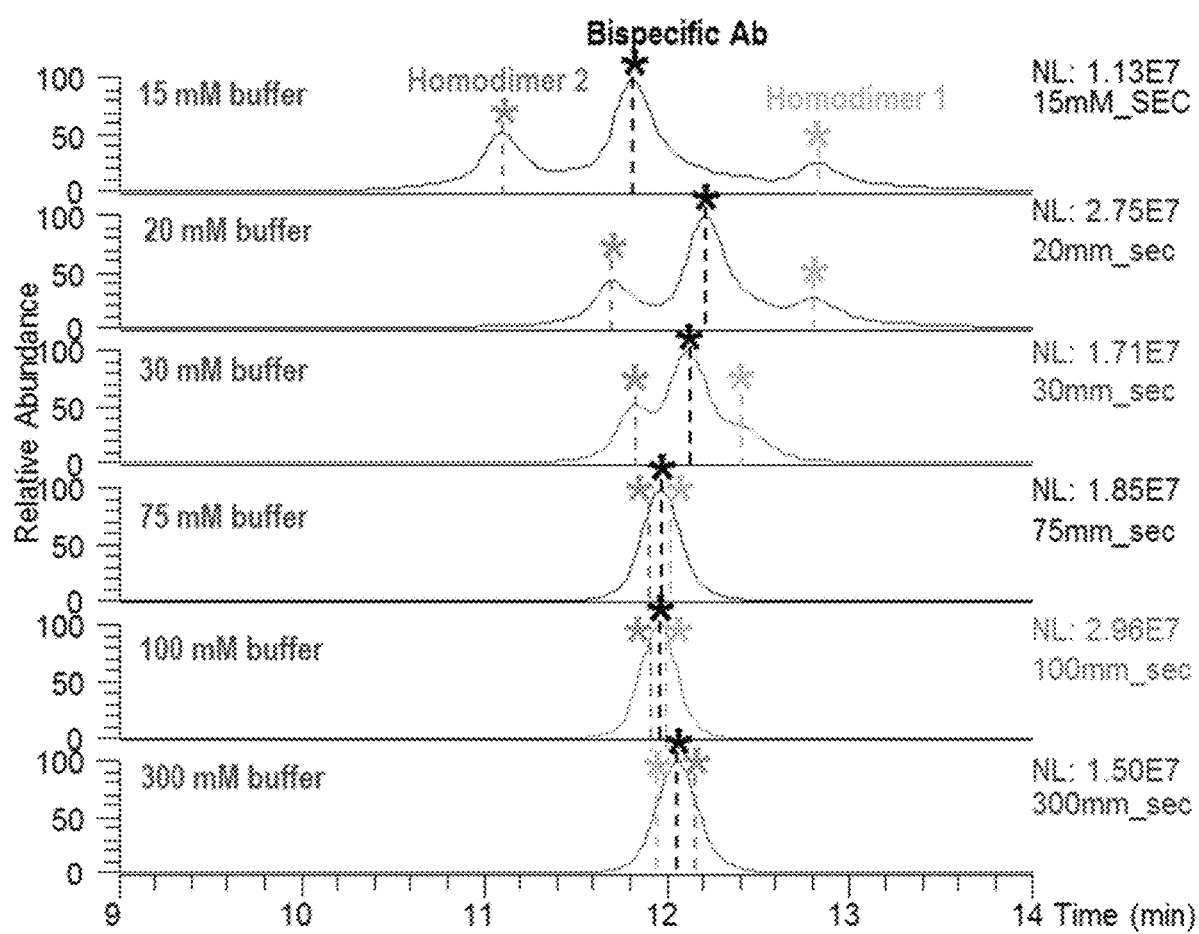
FIG. 16 shows the extracted ion chromatograms (XIC) obtained on conducting MM-SEC-MS analysis of deglycosylated mixture of bispecific antibody, homodimer 1, and homodimer 2 on Waters BEH SEC Column according to an exemplary embodiment.
Figure 17:
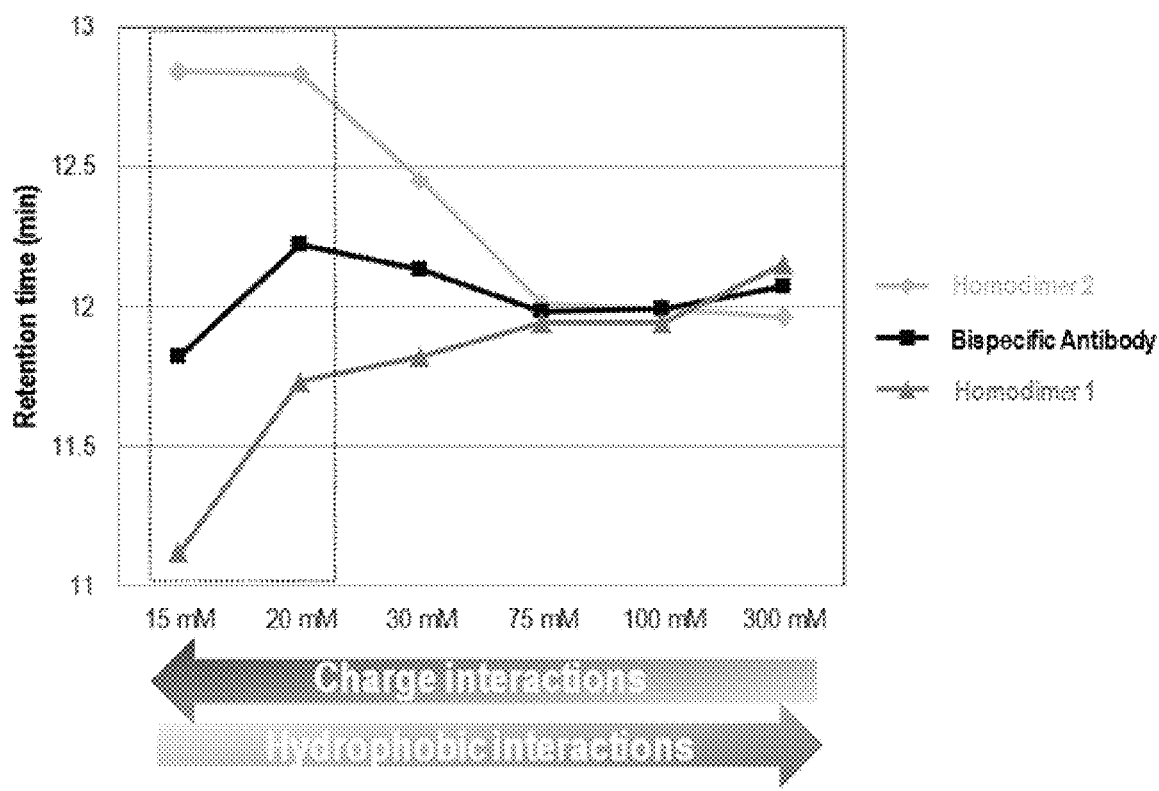
FIG. 17 shows the chart of retention time (minutes) of a protein vs. total salt concentration of the mobile phase for a deglycosylated mixture of bispecific antibody, homodimer 1, and homodimer 2 on performing MM-SEC-MS analysis on Waters BEH SEC Column according to an exemplary embodiment.

The use of 15 mM total salt concentration shows significant separation of the homodimer 1, bispecific antibody, and homodimer 2. At 15 mM salt concentration, homodimer 2 had a earlier retention time than the bispecific antibody, which showed an earlier retention time than homodimer 1. On increasing the concentration of the mobile phase, the differences in the retention times reduced. Further, at salt concentration of 300 mM of the mobile phase, homodimer 1 had a earlier retention time than the bispecific antibody, which showed a earlier retention time than homodimer 2 (See FIG. 16 and FIG. 17). As described in FIG. 14 and FIG. 15, this effect is due to the development of an additional interaction on the SEC column. The additional interaction depends on the salt concentration of the mobile phase. At lower concentrations, the charge-charge interactions are predominant on the column and determine the retention of the proteins on the column.

Example 9. MM-SEC-MS Analysis of an IgG1 Molecule and its Oxidized Variant on Waters BEH SEC Column 9.1 Preparation of an Oxidized Variant of an IgG1 Molecule—Ab1

Ab1 was treated with peptide N-glycosidase F (PNGase F; 1 IUB milliunit per 10 µg of protein) at 45° C. for 1 hour to completely remove the glycan chains from each heavy chain constant region.

9.2 MINI-SEC-MS

The acquisition using MM-SEC-MS was performed isocratically using a Waters BEH SEC Colum on the system as described above. Elution was monitored by UV at 280 nm.

Three set of experiments were carried out. In the first experiment, the mobile phase comprised 93.3 mM ammonium acetate and 6.7 mM ammonium bicarbonate, in the second experiment, the mobile phase comprised 140 mM ammonium acetate and 10 mM ammonium bicarbonate, and in the third experiment, the sixth experiment, the mobile phase comprised 280 mM ammonium acetate and 20 mM ammonium bicarbonate. The elution was carried out at a flow rate of 0.2 mL/min.

For analytical runs, the injection loads consisted of 10 μg of the protein.

Figure 18:
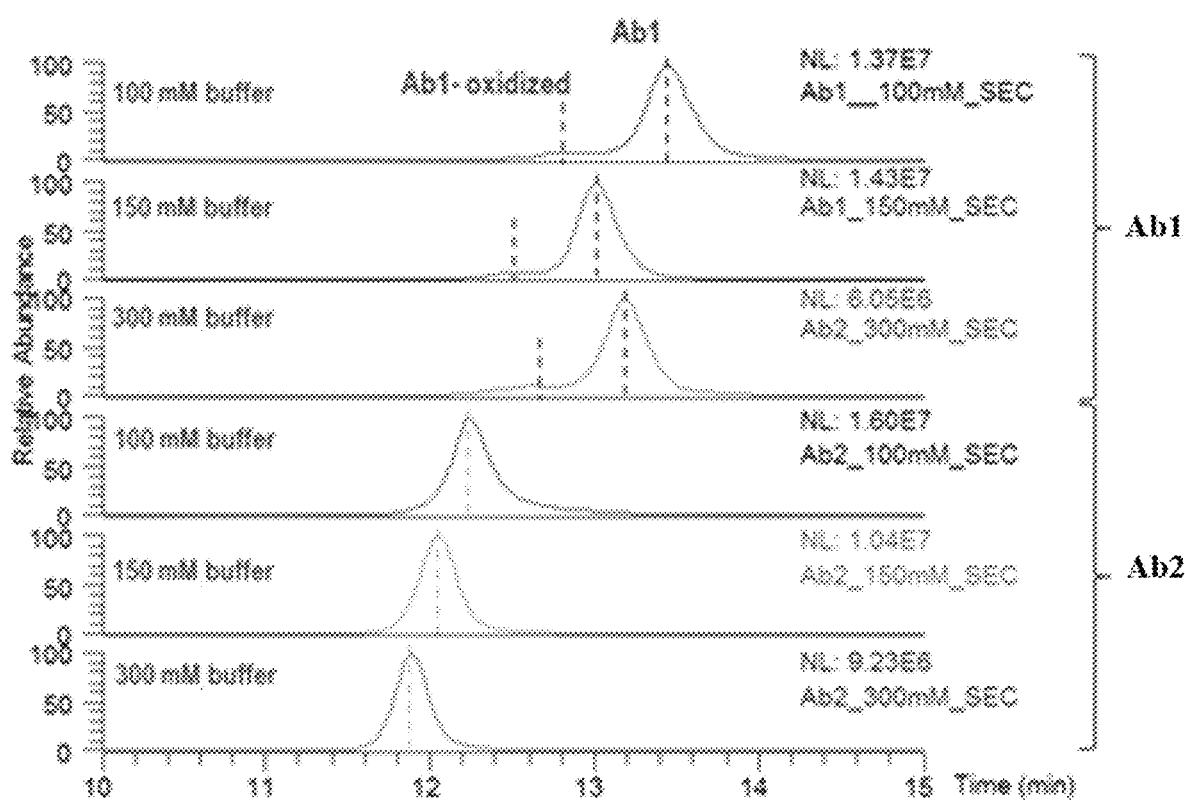
FIG. 18 shows the extracted ion chromatograms (XIC) obtained on conducting MM-SEC-MS analysis of an antibody and its oxidized variant on Waters BEH SEC Column according to an exemplary embodiment.

There is a significant separation of the antibody Ab1 and its oxidized variant on MM-SEC-MS system on using 100 mM, 150 mM, and 300 mM salt concentration of the mobile phase (See FIG. 18, top panel). The pI of the IgG1 antibody Ab1 is 8.65. For IgG1 molecules with higher PI, charge interaction plays a more dominant role compared to IgG4 molecules, which have low pI values.

Example 10. MM-SEC-MS Analysis of an IgG1 Molecule on Waters BEH SEC Column 10.1 Preparation of the IgG1 Molecule—Ab2

Ab2 was treated with peptide N-glycosidase F (PNGase F; 1 IUB milliunit per 10 μg of protein) at 45° C. for 1 hour to completely remove the glycan chains from each heavy chain constant region.

10.2 MINI-SEC-MS

The acquisition using MM-SEC-MS was performed isocratically using a Waters BEH SEC Colum on the system as described in Example 8.2. Comparing the retention times of the two IgG1 molecules—Ab1 and Ab2, it was observed that the Ab2 molecule had lower retention times (See FIG. 18, bottom panel).

Figure 19:
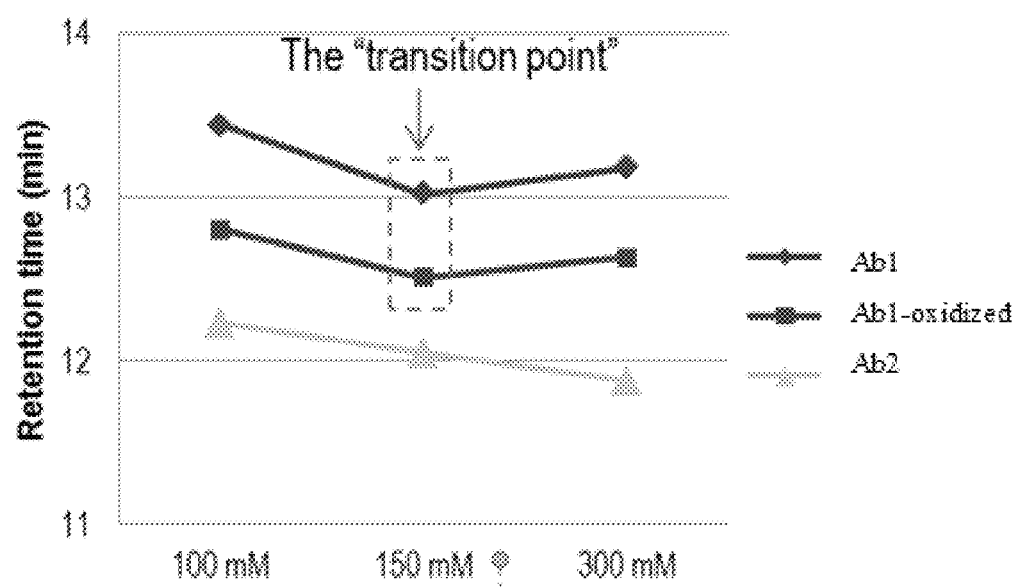
FIG. 19 shows the chart of retention time (minutes) of a protein vs. total salt concentration of the mobile phase for an antibody and its oxidized variant on performing MM-SEC-MS analysis on Waters BEH SEC Column according to an exemplary embodiment.

This can be explained due to hydrophobicity difference between Ab1 and Ab2. For more hydrophobic molecules, the "salting out" effect starts to occur at lower salt concentration compared to the less hydrophobic molecules. This point is also referred to as the transition point (See FIG. 19).

Figure 20:
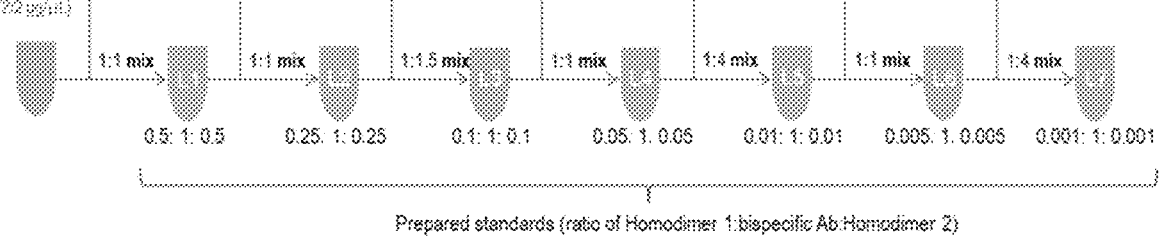
FIG. 20 shows a method of sample preparation of the mixture containing bispecific antibody and its homodimer species according to an exemplary embodiment.

Example 11. Quantification of Homodimer Impurities in the Bispecific Antibody Using MM-SEC-MS The standards were generated using the methodology illustrated in FIG. 20.

Figure 21:
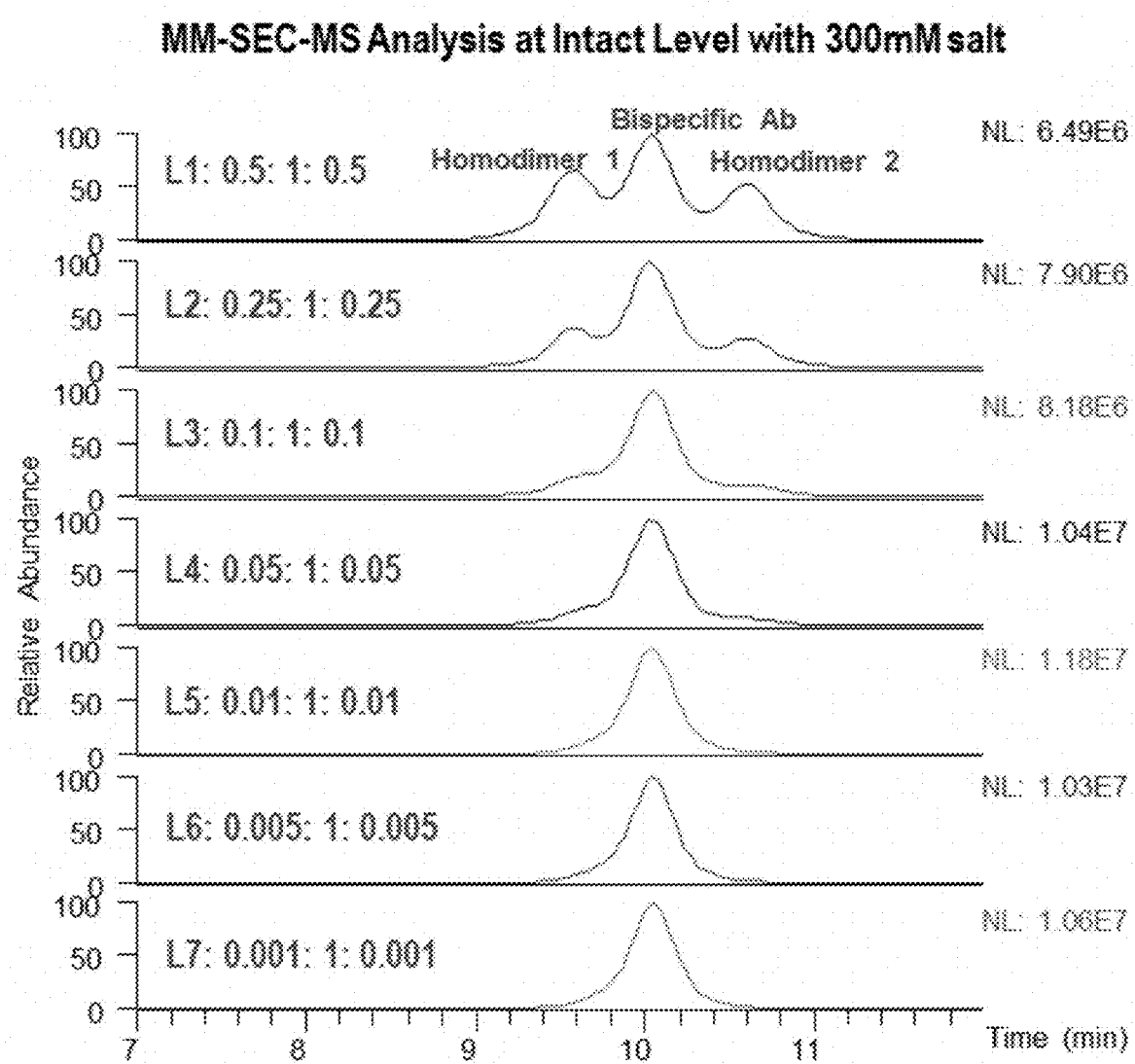
FIG. 21 shows MINI-SEC-MS analysis of mixture at intact level of bispecific antibody and its homodimer species using mobile phase with 300 mM salt concentration according to an exemplary embodiment.
Figure 22:
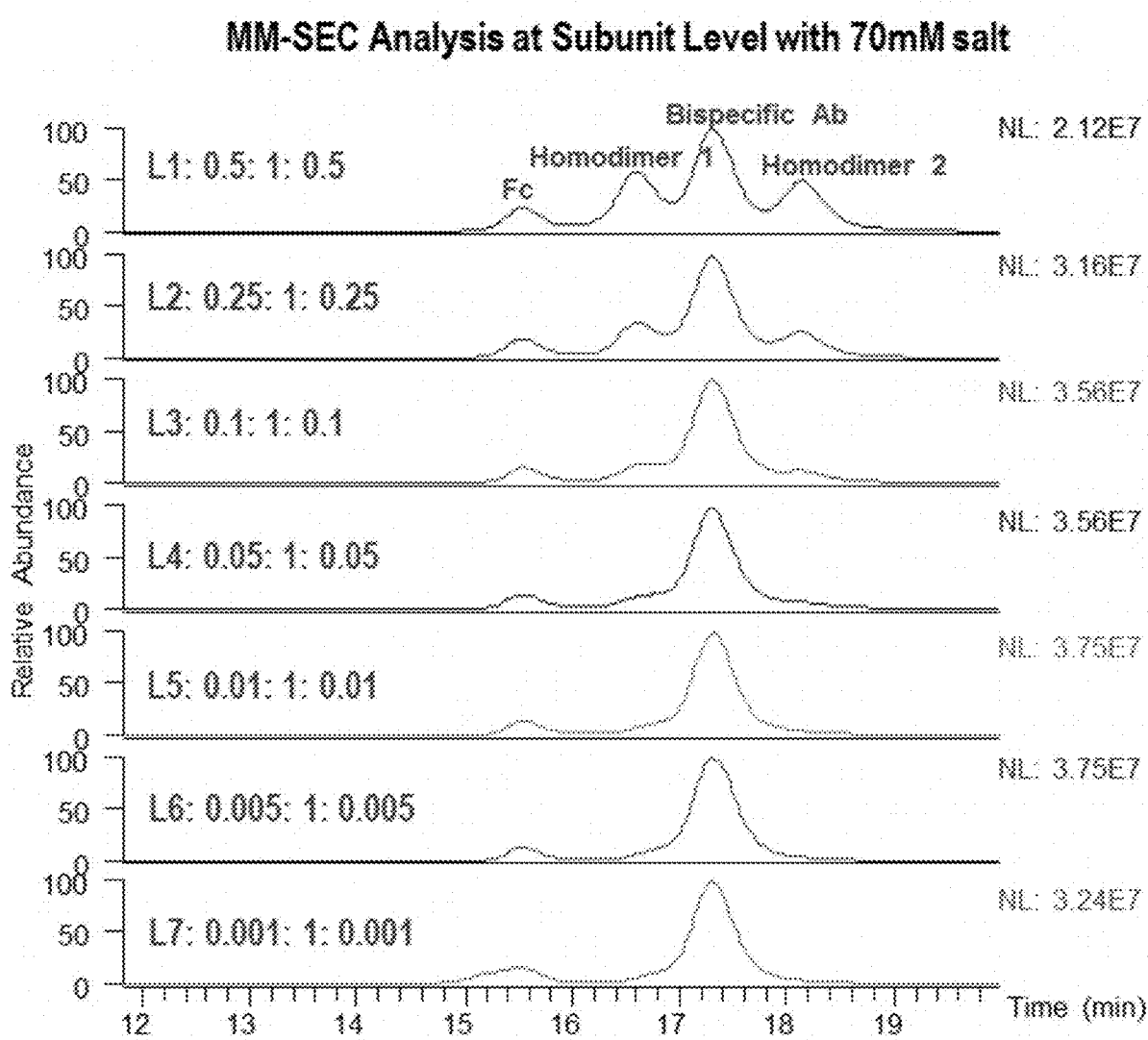
FIG. 22 shows MINI-SEC-MS analysis of mixture at subunit level of bispecific antibody and its homodimer species using mobile phase with 70 mM salt concentration according to an exemplary embodiment.

The acquisition using MM-SEC-MS was performed isocratically using a Zenix SEC-300 MK column (4.6×300 nm, 3 μm) Column on the system as described. The mobile phases with 300 mM salt concentration and 70 mM salt concentration were used to elute the proteins. For both the concentrations in intact as well as subunit level, higher detection using MM-SEC-MS was observed in samples with higher amount of homodimers (See FIG. 21 and FIG. 22). At 70 mM salt concentration for mobile phase, an additional Fc impurity of the bispecific antibody was also detected.

Figure 23:
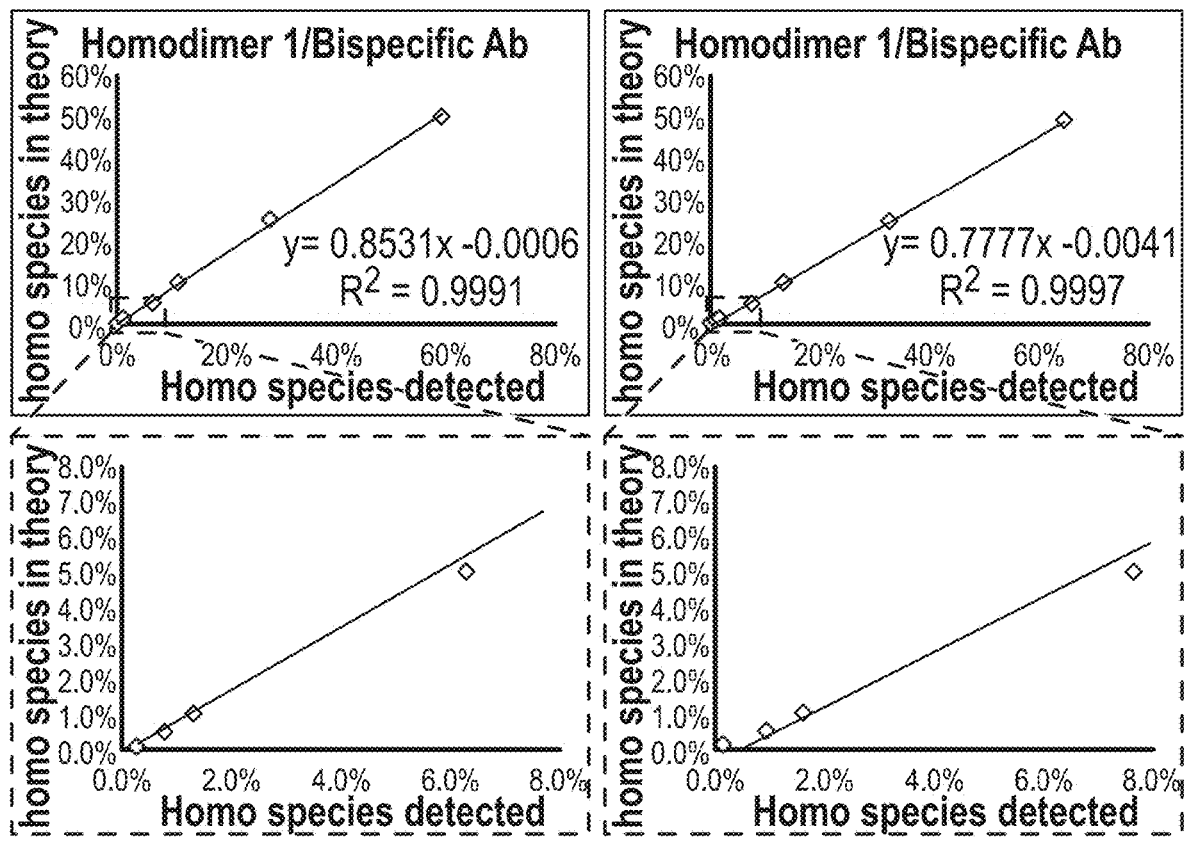
FIG. 23 shows the homodimer quantitation results from MM-SEC-MS analysis at intact level of bispecific antibody and its homodimer species according to an exemplary embodiment.

At intact level, the plot of homodimer 1/bispecific antibody theoretical vs. homodimer 1/bispecific antibody detected and of homodimer 2/bispecific antibody theoretical vs. homodimer 2/bispecific antibody detected showed a good linearity for quantification of homodimers present from 0.1% to 50% (See FIG. 23).

Figure 24:
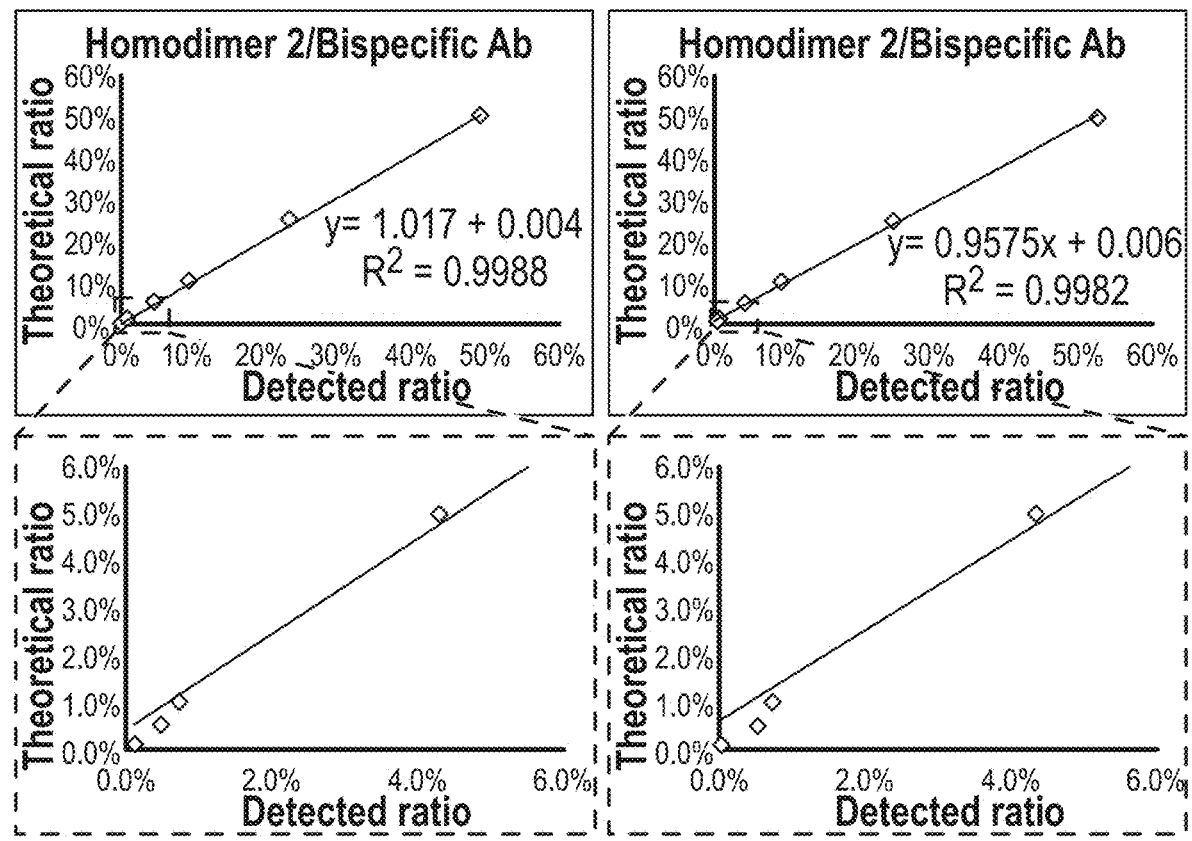
FIG. 24 shows the homodimer quantitation results from MM-SEC-MS analysis at subunit level of bispecific antibody and its homodimer species according to an exemplary embodiment.

At subunit level, the plot of homodimer 1/bispecific antibody theoretical vs. homodimer 1/bispecific antibody detected and of homodimer 2/bispecific antibody theoretical vs. homodimer 2/bispecific antibody detected showed a good linearity for quantification of homodimers present from 0.1% to 50% (See FIG. 24). Compared to the intact level, better accuracy was obtained at the subunit level.

Example 12. Mixed-Mode SEC Separation of Bispecific and Homodimer Antibodies for Native MS Detection Four bsAb molecules with different pI values and hydrophobicity (Table 3) were mixed with their corresponding homodimer antibodies and used as the testing standards. Each bsAb molecule (HH*L2) contains two identical light chains (LC) and two different heavy chains (HC and HC*), whereas each homodimer antibody (H2L2 or H*2L2) contains two identical light chains and two identical heavy chains (HC or HC*).

TABLE 3

| | | pI | Hydrophobicity (apparent HIC retention factor*; min) |
|---|---|---|---|
| bsAb2 mixture | bsAb2 (HH*L2) | 6.5 | 5.2 |
| | HC homodimer (H2L2) | 6.1 | 4.3 |
| | HC* homodimer (H*2L2) | 7.2 | 6.1 |
| bsAb3 mixture | bsAb3 (HH*L2) | 7.4 | 4.8 |
| | HC homodimer (H2L2) | 6.6 | 4.2 |
| | HC* homodimer (H*2L2) | 8.3 | 5.6 |
| bsAb4 mixture | bsAb4 (HH*L2) | 7.7 | 7.0 |
| | HC homodimer (H2L2) | 7.3 | 8.4 |
| | HC* homodimer (H*2L2) | 8.0 | 5.7 |
| bsAb5 mixture | bsAb5 (HH*L2) | 8.1 | 6.3 |
| | HC homodimer (H2L2) | 7.4 | 5.2 |
| | HC* homodimer (H*2L2) | 8.5 | 7.7 |

*Apparent HIC retention factor was calculated based on the retention time of the protein molecule analyzed by HIC. A YMC BioPro HIC BF column (4 μm, 100 mm × 4.6 mm) was applied with mobile phase "A" of 3.3M ammonium buffer and mobile phase B of water. A gradient was performed from 100% to 97% A in 18 min at a flow rate of 0.4 mL/min. The apparent HIC retention factor was calculated by normalizing its retention time over 18 min to a scale of 10.

Figure 25:
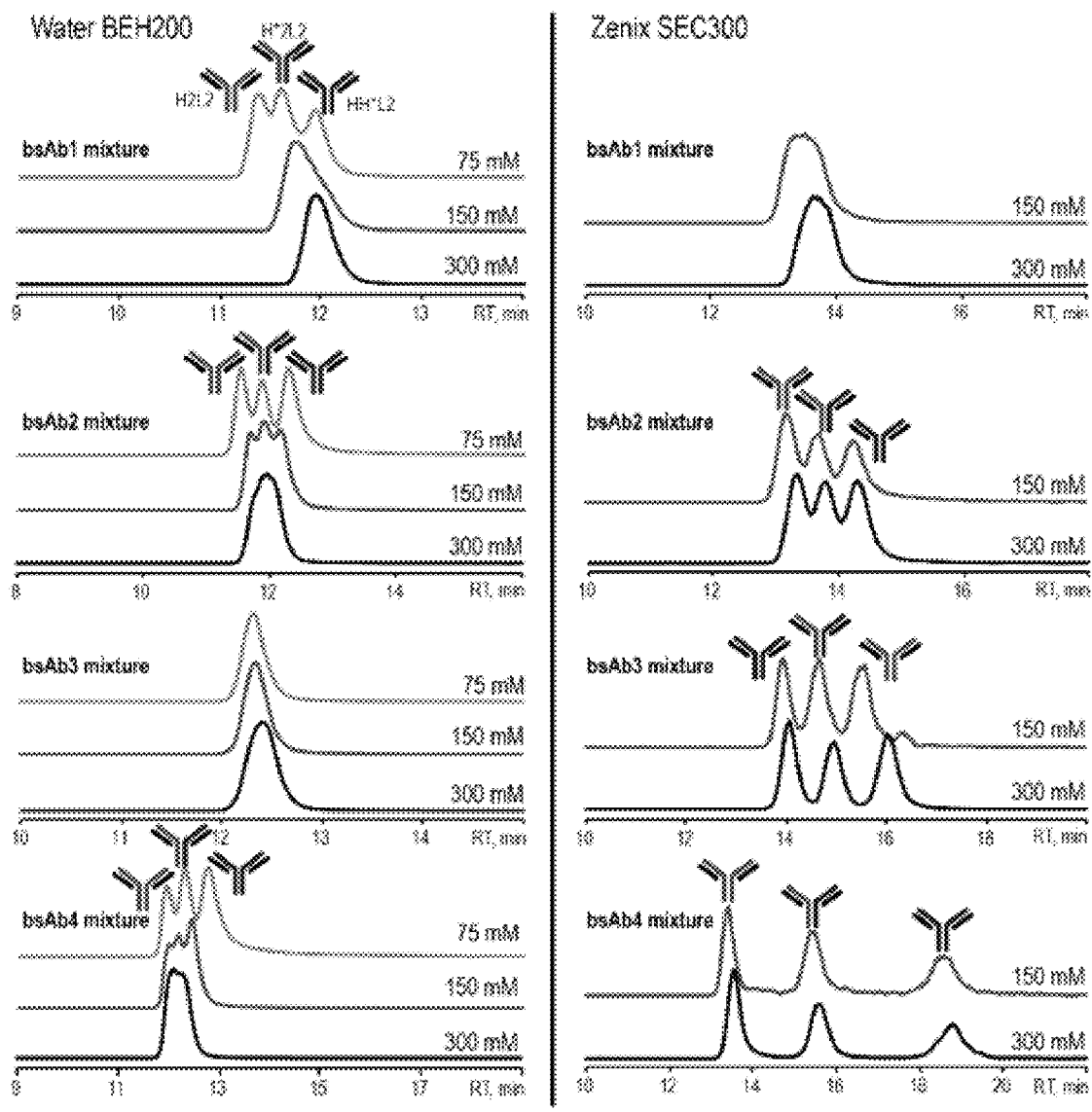
FIG. 25 shows analysis of bispecific antibody mixtures [four different bsAb/H2L2 homodimer/H*2L2 homodimer mixtures] by MINI-SEC-MS on either the BEH column (left) or the Zenix column (right) carried out according to exemplary embodiments, wherein each BPC trace represents one individual analysis using the mobile phase salt concentration indicated.

The four bsAb mixtures were then analyzed on the Waters BEH column using three different salt concentrations (75 mM, 150 mM, and 300 mM), followed by online native MS detection. The resulting base peak chromatograms (BPCs) are shown in the left panels of FIG. 25. Consistent with the observations from the previous study, as the salt concentration increased, mAb molecules with different pI values exhibited different trends in retention times. Taking advantage of the different retention behavior of each antibody at varying salt concentrations, we therefore explored the possibility of separating the homodimers from the bsAb by modulating the salt concentrations. For example, in the bsAb2 mixture, as the salt concentration decreased from 300 mM to 75 mM, the two acidic molecules, H2L2 homodimer (pI=6.1) and HH*L2 bsAb (pI=6.5) both eluted earlier, likely due to reduced hydrophobic and low electrostatic interactions at low salt concentration. In contrast, the neutral molecule, H*2L2 homodimer (pI=7.2), remained almost unchanged in retention time as the salt concentration was modulated, presumably because the reduced hydrophobic interaction was counteracted by the enhanced electrostatic interaction at low salt concentration. In addition, as the H2L2 homodimer exhibited a more significant decrease in retention time compared to the HH*L2 bsAb (possibly due to its lower pI value and thus weaker electrostatic interaction), improved separation between the two was also achieved at a lower salt concentration. As a result, good chromatographic separation between both homodimers and bsAb2 was achieved at 75 mM salt concentration.

Similarly, the separation between bsAb3 and its two homodimers also improved significantly when the salt concentration decreased from 300 mM to 75 mM. This is because the retention times of the H2L2 homodimer (pI=6.6), the HH*L2 bsAb (pI=7.4) and the H*2L2 homodimer (pI=8.3) decreased, remained unchanged, or increased, respectively. It is noteworthy that although baseline resolution was not achieved for either of the two examples, identification and quantitation of homodimers should not be significantly impacted by the co-eluting species as they would be for UV-based quantitation, owing to the high specificity of MS as the detector.

In the bsAb5 mixture, better separation was again achieved at 75 mM salt concentration on the BEH column relative to the high salt condition. This is because the relatively basic molecules, HH*L2 bsAb (pI=8.1) and H*2L2 homodimer (pI=8.5), both exhibited increasingly later retention times, whereas the relatively neutral H2L2 homodimer (pI=7.4) showed no change in retention time as the salt concentration was decreased. However, despite the good chromatographic separation, this condition was not ideal for homodimer quantitation, as peak tailing and protein recovery loss started to occur for the H*2L2 homodimer at the low salt concentration, due to its high basicity. Moreover, the bsAb4 mixture demonstrated that improved separation could not be achieved by decreasing the salt concentration from 300 mM to 75 mM. This is likely because the three molecules all have near neutral pIs (Table 3), and thus exhibit similar retention behavior with corresponding salt concentration changes. Although further lowering the salt concentration to enhance electrostatic interaction may improve the separation, severe peak tailing will likely occur, thus compromising the quantitation. It is also interesting to note that the elution profile of the bsAb4 mixture broadened as the salt concentration increased. At 300 mM salt concentration, the elution order of the three molecules was determined by XICs (data not shown) as H*2L2 homodimer, HH*L2 bsAb, and H2L2 homodimer, which was consistent with their ranking in hydrophobicity determined by hydrophobic interaction chromatography (Table 3). Therefore, further enhancing the hydrophobic interaction by using an even higher salt concentration will likely improve the separation of bsAb4 mixture on this column. Unfortunately, based on our experience, salt concentrations higher than 300 mM usually creates a desolvation issue and significantly impairs native MS sensitivity.

To further examine the separation of the bsAb mixtures, while using salt concentrations favorable for MS analysis, a Sepax Zenix SEC-300 column was evaluated for mixed-mode interactions. The 3 µm silica beads in this column are coated with a chemically bonded, stand-up monolayer, which likely contributes to the moderate hydrophobicity of this column as reported in previous studies (Yang et al, 2016, supra; Wong et al, supra; Pavon et al, supra). At 150 mM and 300 mM salt concentrations, each of the four bsAb mixtures were separated on this column for subsequent native MS detection, and the generated BPCs are shown in the right panels of FIG. 25. As expected, the bsAb4 mixture showed improved separation on the Zenix column compared to the BEH column when operated at the same salt concentrations. The elution order of the three molecules was also consistent with their relative hydrophobicity, with the most hydrophobic H2L2 homodimer eluting last. Note that the chromatographic resolution of the bsAb4 mixture was further improved at 300 mM salt concentration compared to that at 150 mM, which is expected as a higher salt concentration promotes hydrophobic interaction. In addition, the bsAb5 mixture was more effectively resolved on the Zenix column compared to the BEH column, presumably due to the large differences in hydrophobic interaction with the column matrix between mixture components. In summary, by modulating the salt concentration on two SEC columns with different properties, we demonstrate that good chromatographic separation can be achieved for all four bsAb mixtures at salt concentrations favorable for subsequent native MS detection. It is also likely that other SEC columns, not tested in this study, can further extend the applicability of this method, by offering novel mixed-mode interactions.

Example 13. Quantitation of Homodimer Impurities by Native MM-SEC-MS

Figure 26:
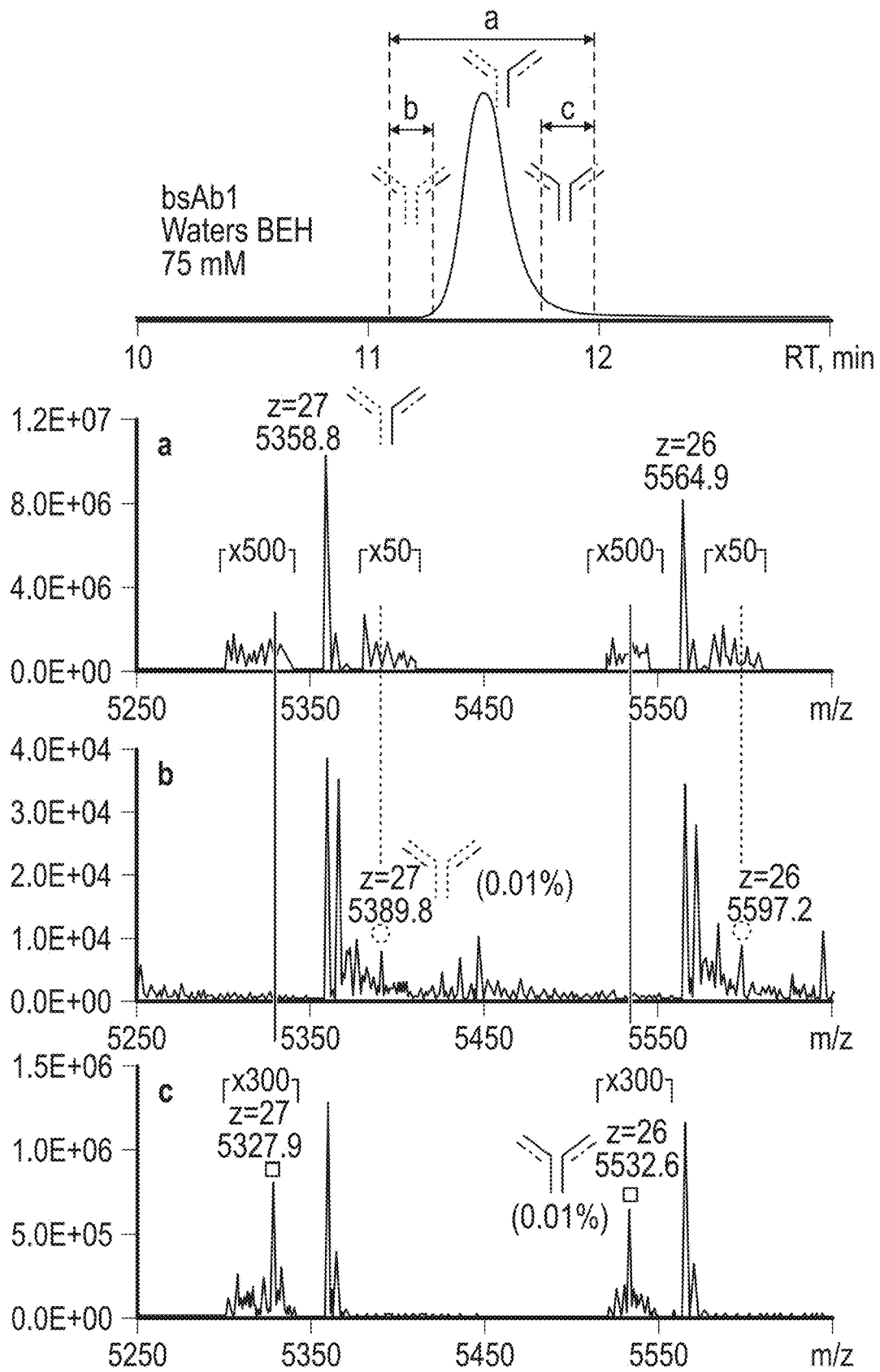
FIG. 26 shows the limit of detection study by MM-SEC-MS for the homodimer impurities in bsAb2 (left panel) and bsAb4 (right panel) using 0.01% and 0.1% spiked-in standards, respectively for analysis carried out according to exemplary embodiments, wherein the native MS spectra (a, b, c, d, e and f) were averaged across the corresponding TIC regions and the two most abundant charge states were shown.
Figure 26:
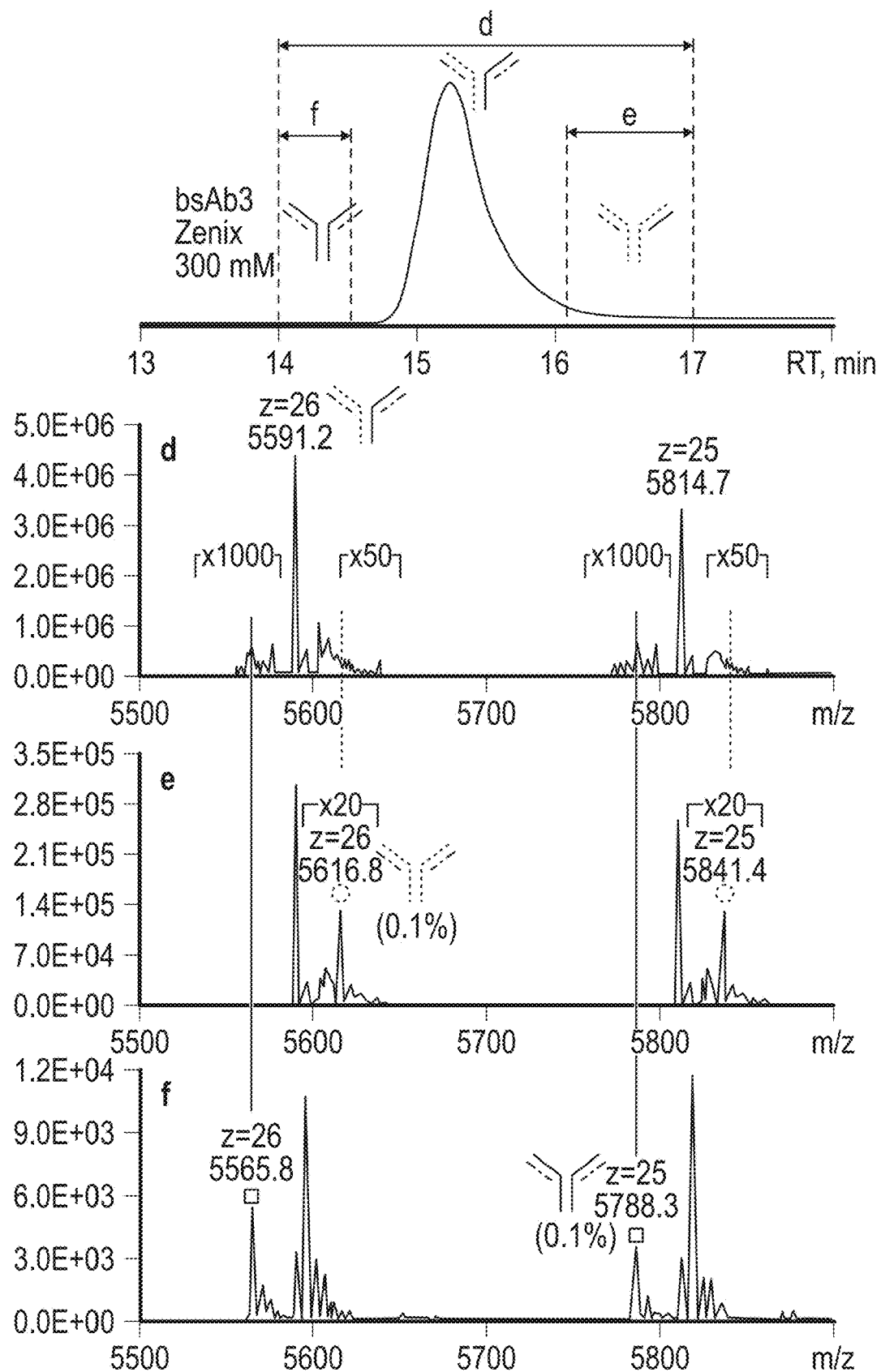
Figure 27:
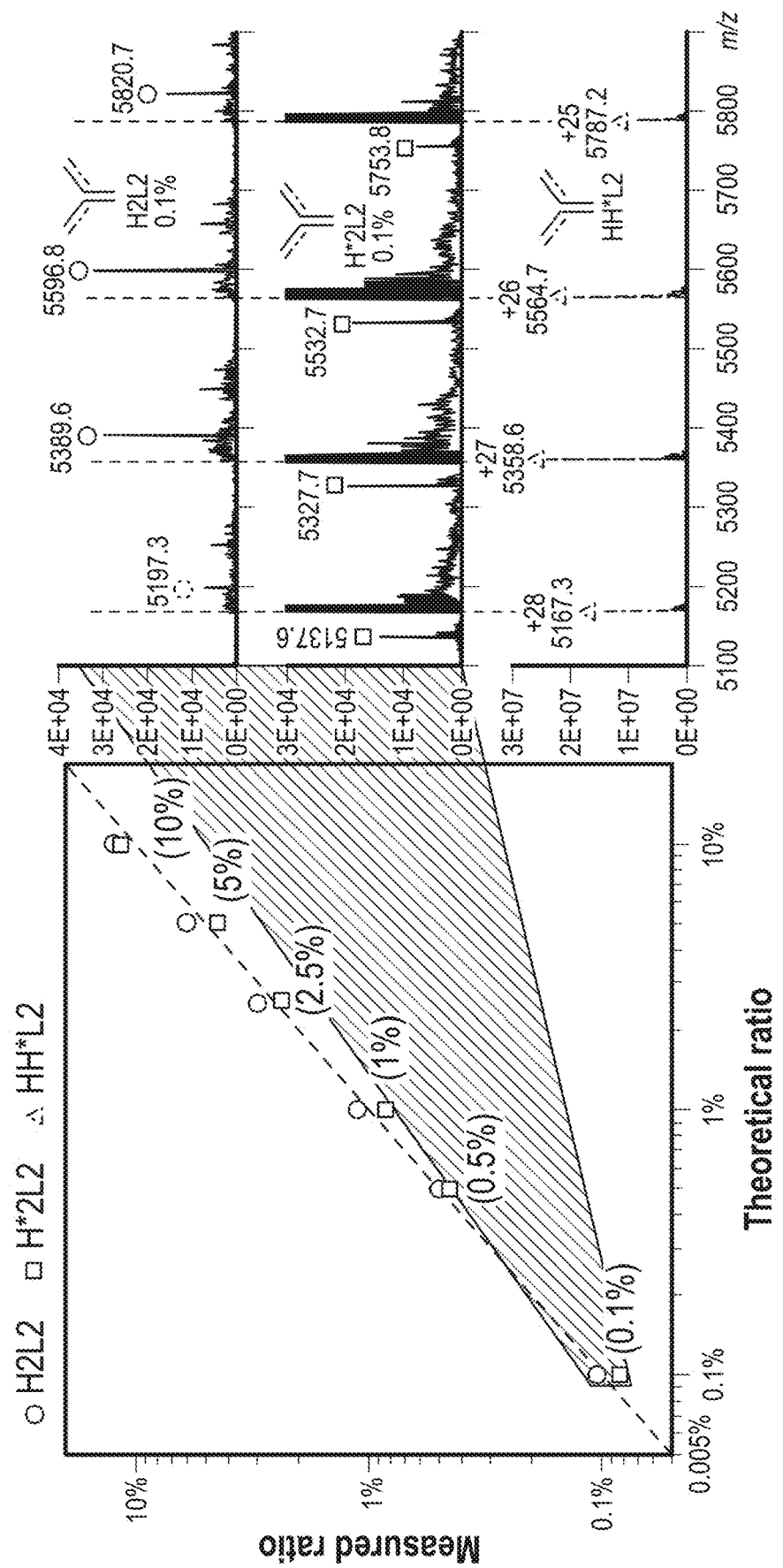
FIG. 27 shows the quantitation study carried out according to exemplary embodiments using homodimers spiked into bsAb2 at serially diluted, known ratios (grey line and the marked values on the left panel) and also shown are the measured ratios of H2L2 homodimer (red) and H*2L2 homodimer (blue) to bsAb2 based on the XIC intensity of the four most abundant charge states in the raw mass spectrum (0.1% relative abundance of each homodimer, as an example shown on the right panel).

Relative quantitation by MS-based approaches often requires a well-characterized understanding of MS response (e.g., ionization efficiency and ion transmission efficiency) from each analyte. Because of the similar size, bsAb and homodimers should exhibit similar ion transmission efficiency during native MS analysis. On the other hand, ionization efficiency could be affected by both the solvent composition at the time of elution and the presence of co-eluting species. As the MM-SEC-MS method utilizes isocratic elution, influences on ionization due to different solvent composition, as commonly seen in gradient elution methods (e.g., IEX-MS), can be eliminated. To evaluate the performance of the MM-SEC-MS method to assess relative quantitation of homodimer impurities, a series of bsAb2 spiked-in samples containing homodimer impurities ranging from relative abundances 0.1% to 10% were prepared for analysis. The Waters BEH column using the 75 mM salt concentration mobile phase was applied to achieve MM-SEC separation between bsAb2 and the corresponding homodimers. To assess the relative quantitation of each homodimer present within the bsAb2 samples, the XICs, based on the m/z of the four most abundant charge states of either homodimer species or bsAb2, were generated and the peak areas were integrated and used for quantitation of the amount of each homodimer. As shown in FIG. 26, reliable quantitation of homodimer impurities ranging from 0.1% to 10% can be readily achieved by this method. In addition, even at a 0.1% spiked-in level, high-quality native mass spectra of both H2L2 and H*2L2 homodimer species can still be obtained (FIG. 27, right panel), leading to high-confidence identification and quantitation.

A novel MM-SEC-MS method has been developed and evaluated for highly sensitive detection and quantitation of homodimer impurities in bsAb samples. We first investigated the mixed-mode interactions between the antibody molecule and the column matrix during SEC separation at different salt concentrations. Using eight distinct antibodies of varying pI, it was observed that under a defined pH condition, the basic molecules exhibited stronger electrostatic interactions with the column matrix compared to the acidic molecules, and such interaction can be enhanced by lowering the salt concentration. On the other hand, increasing the salt concentration during SEC separation can reduce electrostatic interaction, while promoting hydrophobic interactions between the antibody and the column matrix. These mixed-mode interactions provide a unique opportunity for separating antibodies with similar hydrodynamic volume but different surface characteristics. Taking advantage of different column properties, chromatographic separation of four bsAb mixtures was accomplished by the MM-SEC method using either electrostatic interaction or hydrophobic interaction, which was readily achieved by modulating salt concentrations. We also demonstrated that the achieved chromatographic separation was critical to obtain improved detection of low-abundance homodimer impurities by subsequent native MS analysis. In two bsAb examples, homodimer impurities present at 0.01% (bsAb2) and 0.1% (bsAb4) were successfully detected using this MM-SEC-MS method. To the best of our knowledge, this new development represents the most sensitive method in detecting homodimer impurities in bsAb samples. Finally, using a series of spiked-in standards, we demonstrated that the MM-SEC-MS method can deliver reliable quantitation of homodimer impurities present at varying levels. Owing to the high sensitivity, high-confidence identification and quantitation can be obtained even at levels as low as 0.1%. In summary, this newly developed MM-SEC-MS method provides a highly sensitive approach for detection and quantitation of homodimer impurities in bsAb samples and thus can be used to support therapeutic bsAb development. Finally, application of this method might extend to other areas, such as characterization of a mixture of antibodies present in co-formulated therapeutics.

What is claimed is:

1. A method for quantifying a target protein and a protein variant of said target protein in a sample, said method comprising:
   contacting said sample to a chromatographic system having a mixed-mode size exclusion chromatography resin with an additional functionality which results in mixed-mode separation;
   washing the mixed-mode size exclusion chromatography resin using a mobile phase to provide an eluent including the target protein and the protein variant; and
   quantifying the target protein and the protein variant in said eluent using a mass spectrometer.

2. The method of claim 1, wherein the mobile phase has ammonium acetate, ammonium bicarbonate, or ammonium formate, or combinations thereof.

3. The method of claim 1, wherein the mobile phase has a total concentration of less than about 600 mM of ammonium acetate and ammonium bicarbonate.

4. The method of claim 1, wherein the mobile phase has a flow rate of about 0.2 ml/min—about 0.4 ml/min.

5. The method of claim 1, wherein the amount of the sample loaded onto the mixed-mode size exclusion chromatography resin is about 10 µg to about 100 µg.

6. The method of claim 1, wherein the target protein is a bispecific antibody.

7. The method of claim 1, wherein the target protein is a therapeutic antibody.

8. The method of claim 1, wherein the mass spectrometer is coupled to the chromatographic system.

9. The method of claim 1, wherein the additional functionality is a hydrophobic interaction functionality.

10. The method of claim 1, wherein the additional functionality is a charge-charge interaction functionality.

11. The method of claim 1, wherein the mass spectrometer is a native mass spectrometer.

12. A method for detecting a target protein in a sample, said method comprising:
    contacting said sample to a chromatographic system having a mixed-mode size exclusion chromatography resin with an additional functionality which results in mixed-mode separation;
    washing the mixed-mode size exclusion chromatography resin using a mobile phase to provide an eluent including the target protein; and
    detecting the target protein in said eluent using a mass spectrometer.

13. The method of claim 12, wherein the mobile phase used to elute the target protein has ammonium acetate, ammonium bicarbonate, or ammonium formate, or combinations thereof.

14. The method of claim 12, wherein the mobile phase used to elute the target protein has a total concentration of less than about 600 mM of ammonium acetate and ammonium bicarbonate.

15. The method of claim 12, wherein the mass spectrometer is coupled to the chromatographic system.

16. The method of claim 12, wherein the additional functionality is a hydrophobic interaction functionality.

17. The method of claim 12, wherein the additional functionality is a charge-charge interaction functionality.

18. The method of claim 12, wherein the mass spectrometer is a native mass spectrometer.

19. The method of claim 12, wherein the target protein is a bispecific antibody.

20. The method of claim 12, wherein the target protein is a therapeutic antibody.

* * * * *